United States Patent
Haruta et al.

(10) Patent No.: US 7,960,407 B2
(45) Date of Patent: Jun. 14, 2011

(54) CRYSTAL FORMS OF AN IMIDAZOLE DERIVATIVE

(75) Inventors: Naoaki Haruta, Handa (JP); Tomoki Kato, Ichihara (JP); Zheng Jane Li, Southbury, CT (US); Toyoharu Numata, Chita-gun (JP); Andrew Vincent Trask, New York, NY (US)

(73) Assignee: Requalia Pharma Inc., Aichi-Ken (JP)

( * ) Notice: Subject to any disclaimer, the term of this patent is extended or adjusted under 35 U.S.C. 154(b) by 357 days.

(21) Appl. No.: 11/908,163

(22) PCT Filed: Mar. 1, 2006

(86) PCT No.: PCT/IB2006/000754
§ 371 (c)(1),
(2), (4) Date: Sep. 11, 2008

(87) PCT Pub. No.: WO2006/095268
PCT Pub. Date: Sep. 14, 2006

(65) Prior Publication Data
US 2009/0018158 A1    Jan. 15, 2009

(51) Int. Cl.
*C07D 487/04* (2006.01)
*A61K 31/437* (2006.01)
*A61P 29/00* (2006.01)
*A61P 37/00* (2006.01)
*A61P 19/02* (2006.01)

(52) U.S. Cl. ......................................... 514/303; 546/118

(58) Field of Classification Search .................. 546/118; 514/303
See application file for complete search history.

(56) References Cited

FOREIGN PATENT DOCUMENTS
WO          02/32422    *   4/2002
WO       WO 0232900        4/2002

OTHER PUBLICATIONS

Caira, M.R., Topics in Current Chemistry, vol. 198, p. 163-208, "Crystalline Polymorphism of Organic Compounds."

* cited by examiner

*Primary Examiner* — D. Seaman
*Assistant Examiner* — Niloofar Rahmani
(74) *Attorney, Agent, or Firm* — Scully, Scott, Murphy & Presser, P.C.

(57) ABSTRACT

The invention relates to the essentially pure N-[({2-[4-(2-Ethyl-4,6-dimethyl-1H-imidazo[4,5-c]pyridin-1-yl)phenyl]ethyl}amino)carbonyl]-4-methylbenzenesulfonamide Polymorph Forms A and B and to processes for the preparation of, compositions containing and to the uses of, such crystal forms.

8 Claims, 8 Drawing Sheets

N-[({2-[4-(2-Ethyl-4,6-dimethyl-1H-imidazo[4,5-c]pyridin-1-yl)phenyl]ethyl}amino)carbonyl]-4-methylbenzenesulfonamide Form A N-[({2-[4-(2-Ethyl-4,6-dimethyl-1H-imidazo[4,5-c]pyridin-1-yl)phenyl]ethyl}amino)carbonyl]-4-methylbenzenesulfonamide Form B N-[({2-[4-(2-Ethyl-4,6-dimethyl-1H-imidazo[4,5-c]pyridin-1-yl)phenyl]ethyl}amino)carbonyl]-4-methylbenzenesulfonamide Form C N-[({2-[4-(2-Ethyl-4,6-dimethyl-1H-imidazo[4,5-c]pyridin-1-yl)phenyl]ethyl}amino)carbonyl]-4-methylbenzenesulfonamide Form D N-[({2-[4-(2-Ethyl-4,6-dimethyl-1H-imidazo[4,5-c]pyridin-1-yl)phenyl]ethyl}amino)carbonyl]-4-methylbenzenesulfonamide Form G PXRD of N-[({2-[4-(2-Ethyl-4,6-dimethyl-1H-imidazo[4,5-c]pyridin-1-yl)phenyl]ethyl}amino)carbonyl]-4-methylbenzenesulfonamide polymorphs. (upper: Polymorph Form A, middle: Polymorph Form B, lower: WO 02/32900, Example 42, Step 8, reference )

CRYSTAL FORMS OF AN IMIDAZOLE DERIVATIVE

The present invention relates to novel crystal forms of N-[({2-[4-(2-ethyl-4,6-dimethyl-1H-imidazo[4,5-c]pyridin-1-yl)phenyl]ethyl}amino)carbonyl]-4-methylbenzenesulfonamide (alternatively named 2-Ethyl-4,6-dimethyl-1-(4-{2-[({[(4-methylphenyl)sulfonyl]amino}carbonyl)amino]ethyl}phenyl)-1H-imidazo[4,5-c]pyridine).

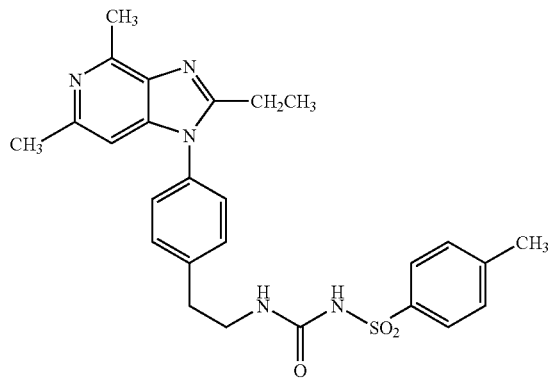

More particularly, the invention relates to the polymorph forms known as A and B, and to processes for the preparation of, compositions containing and to uses of, such polymorphs.

N-[({2-[4-(2-Ethyl-4,6-dimethyl-1H-imidazo[4,5-c]pyridin-1-yl)phenyl]ethyl}amino)carbonyl]-4-methylbenzenesulfonamide is disclosed in WO-A-02/32900 as an EP4 receptor antagonist, which is useful in the treatment or alleviation of pain and inflammation and other inflammation-associated disorders, such as arthritis, in particular osteoarthritis.

The use of N-[({2-[4-(2-Ethyl-4,6-dimethyl-1H-imidazo[4,5-c]pyridin-1-yl)phenyl]ethyl}amino)carbonyl]-4-methylbenzenesulfonamide in the treatment of rheumatoid arthritis is also disclosed in WO-A-02/32422. Furthermore, the use of N-[({2-[4-(2-Ethyl-4,6-dimethyl-1H-imidazo[4,5-c]pyridin-1-yl)phenyl]ethyl}amino)carbonyl]-4-methylbenzenesulfonamide in the treatment of IL-6 involved diseases, such as alcoholic cirrhosis, amyloidosis, atherosclerosis, cardiac disease, sclerosis and organ transplantation reactions, is disclosed in WO-A-03/086371.

The previously known methods of preparing N-[({2-[4-(2-Ethyl-4,6-dimethyl-1H-imidazo[4,5-c]pyridin-1-yl)phenyl]ethyl}amino)carbonyl]-4-methylbenzenesulfonamide, described in WO-A-02/32900, have produced an unstable solvate, which may be an isomorphic form of crystal form C.

It is an object of this invention to provide a pharmaceutically suitable, essentially pure, crystalline, crystal form of N-[({2-[4-(2-Ethyl-4,6-dimethyl-1H-imidazo[4,5-c]pyridin-1-yl)phenyl]ethyl}amino)carbonyl]-4-methylbenzenesulfonamide that can be easily, economically and reproducibly prepared for use in a pharmaceutical formulation having consistent performance characteristics such as relating to stability and bioavailability.

It has now been surprisingly found that this object has been achieved by the present invention, which provides essentially pure, crystalline polymorphic forms of N-[({2-[4-(2-Ethyl-4,6-dimethyl-1H-imidazo[4,5-c]pyridin-1-yl)phenyl]ethyl}amino)carbonyl]-4-methylbenzenesulfonamide known as Polymorph Form A and Polymorph Form B, and an inventive process for the preparation of each thereof. Polymorph Form A was found to be the most stable of the forms identified. It is anhydrous, crystalline, non-hygroscopic, high-melting and has acceptable solid-state properties for solid dosage form development. Polymorph Form B was also found to be stable and suitable for use in a pharmaceutical formulation.

Accordingly, the present invention provides essentially pure, crystalline, N-[({2-[4-(2-Ethyl-4,6-dimethyl-1H-imidazo[4,5-c]pyridin-1-yl)phenyl]ethyl}amino)carbonyl]-4-methylbenzenesulfonamide Polymorph Form A, which is characterised by a powder X-ray diffraction pattern (PXRD) obtained by irradiation with Cu Kα radiation which includes main peaks at 2-Theta° 9.8, 13.2, 13.4, 13.7, 14.1, 17.5, 19.0, 21.6, 24.0 and 25.7+/−0.2.

N-[({2-[4-(2-Ethyl-4,6-dimethyl-1H-imidazo[4,5-c]pyridin-1-yl)phenyl]ethyl}amino)carbonyl]-4-methylbenzenesulfonamide Polymorph Form A is further characterised by differential scanning calorimetry (DSC) in which it exhibits an endothermic thermal event at about 160° C.

N-[({2-[4-(2-Ethyl-4,6-dimethyl-1H-imidazo[4,5-c]pyridin-1-yl)phenyl]ethyl}amino)carbonyl]-4-methylbenzenesulfonamide Polymorph Form A is yet further characterised by an infrared (IR) spectrum (KBr) which shows absorption bands at 2985, 2920, 2871, 1706, 1641, 1596, 1515, 1456, 1369, 1340, 1294, 1249, 1224, 1164, 1124, 1091, 1016, 902, 815, 659, 574 and 549 cm$^{-1}$.

The present invention further provides essentially pure, crystalline, N-[({2-[4-(2-Ethyl-4,6-dimethyl-1H-imidazo[4,5-c]pyridin-1-yl)phenyl]ethyl}amino)carbonyl]-4-methylbenzenesulfonamide Polymorph Form B, which is characterised by a powder X-ray diffraction pattern obtained by irradiation with Cu Kα radiation which includes main peaks at 2-Theta° 6.3, 11.3, 12.8, 13.0, 13.5, 14.5, 15.6, 20.5, 23.0, and 25.8+/−0.2.

N-[({2-[4-(2-Ethyl-4,6-dimethyl-1H-imidazo[4,5-c]pyridin-1-yl)phenyl]ethyl}amino)carbonyl]-4-methylbenzenesulfonamide Polymorph Form B is further characterised by differential scanning calorimetry (DSC) in which it exhibits an endothermic event at about 178° C.

N-[({2-[4-(2-Ethyl-4,6-dimethyl-1H-imidazo[4,5-c]pyridin-1-yl)phenyl]ethyl}amino)carbonyl]-4-methylbenzenesulfonamide Polymorph Form B is yet further characterised by an infrared (IR) spectrum (KBr) which shows unique absorption bands at 3443, 3296 and 1704 cm$^{-1}$.

Further described are the essentially pure, crystalline, N-[({2-[4-(2-Ethyl-4,6-dimethyl-1H-imidazo[4,5-c]pyridin-1-yl)phenyl]ethyl}amino)carbonyl]-4-methylbenzenesulfonamide Crystal Forms C, D, and G. It will be appreciated that these Crystal Forms are not to be regarded only as synthetic intermediates that can be further processed to N-[({2-[4-(2-Ethyl-4,6-dimethyl-1H-imidazo[4,5-c]pyridin-1-yl)phenyl]ethyl}amino)carbonyl]-4-methylbenzenesulfonamide Polymorph Forms A and B, but they also have the same therapeutic properties. However N-[({2-[4-(2-Ethyl-4,6-dimethyl-1H-imidazo[4,5-c]pyridin-1-yl)phenyl]ethyl}amino)carbonyl]-4-methylbenzenesulfonamide Crystal Forms C, D and G are not as suitable as Polymorph Forms A and B for use in preparing pharmaceutical formulations, principally because the former Crystal Forms are less stable.

N-[({2-[4-(2-Ethyl-4,6-dimethyl-1H-imidazo[4,5-c]pyridin-1-yl)phenyl]ethyl}amino)carbonyl]-4-methylbenzenesulfonamide Crystal Forms C, D and G are characterised by PXRD and differential scanning calorimetry (DSC), as detailed in Table 1:

TABLE 1

| Form | DSC endotherm | PXRD peaks at 2-Theta ° +/− 0.2 |
|---|---|---|
| C | 127° C., 161° C. (metastable) | 6.6, 7.1, 7.5, 9.0, 9.5, 9.9, 10.8, 11.5, 12.1, 12.5, 13.3, 14.4, 15.2, 15.4, 16.0, 16.4, 16.8, 17.2, 17.8, 18.2, 19.2, 19.9, 20.6, 21.6, 22.1, 22.4, 22.7, 23.2, 23.6, 24.0, 24.6, 25.0, 25.9, 26.6, 27.1, 27.5, 27.9, 28.5, 29.0, 30.4, 30.7, 32.4, 32.6, 37.8 |
| D | 109° C., 132° C., 144° C., 163° C. | 7.2, 7.6, 9.6, 11.1, 12.6, 13.5, 14.4, 15.1, 15.4, 15.7, 16.1, 17.8, 18.3, 19.2, 19.8, 20.7, 21.0, 21.4, 21.9, 22.4, 22.8, 23.4, 23.8, 24.6, 24.7, 26.0, 27.2, 27.5, 28.3, 28.6, 28.9, 30.3, 31.0, 31.7, 32.5, 32.8, 33.5, 34.0, 34.3, 36.2 |
| G | 130° C., 156° C. ± 5 | 7.2, 10.0, 13.4, 14.1, 14.6, 15.3, 16.1, 17.3, 18.3, 19.6, 20.1, 21.6, 22.8, 23.1, 23.9, 24.8, 24.9, 25.7, 26.0, 26.4, 27.9, 30.7 |

The expression 'essentially pure' when used herein means at least 95% by weight purity. More preferably, 'essentially pure' means at least 98% by weight purity and most preferably means at least 99% by weight purity.

As a further aspect of the invention, there is provided N-[({2-[4-(2-Ethyl-4,6-dimethyl-1H-imidazo[4,5-c]pyridin-1-yl)phenyl]ethyl}amino)carbonyl]-4-methylbenzenesulfonamide Polymorph Form A or B for use as a medicament.

As a yet further aspect of the invention, there is provided the use of N-[({2-[4-(2-Ethyl-4,6-dimethyl-1H-imidazo[4,5-c]pyridin-1-yl)phenyl]ethyl}amino)carbonyl]-4-methylbenzenesulfonamide Polymorph Form A or B in the manufacture of a medicament for the treatment of any disease for which an EP4 receptor antagonist is indicated, particularly for the curative, prophylactic or palliative treatment of pain, inflammation, osteoarthritis or rheumatoid arthritis.

As an alternative aspect, there is provided a method for the treatment of any disease for which an EP4 receptor antagonist is indicated, particularly for the curative, prophylactic or palliative treatment of pain, inflammation, osteoarthritis or rheumatoid arthritis, including administration of a therapeutically effective amount of N-[({2-[4-(2-Ethyl-4,6-dimethyl-1H-imidazo[4,5-c]pyridin-1-yl)phenyl]ethyl}amino)carbonyl]-4-methylbenzenesulfonamide Polymorph Form A or B to a mammal, including a human, in need of such treatment.

The N-[({2-[4-(2-Ethyl-4,6-dimethyl-1H-imidazo[4,5-c]pyridin-1-yl)phenyl]ethyl}amino)carbonyl]-4-methylbenzenesulfonamide Polymorph Forms A and B of the present invention are useful for the general treatment of pain.

Physiological pain is an important protective mechanism designed to warn of danger from potentially injurious stimuli from the external environment. The system operates through a specific set of primary sensory neurones and is activated by noxious stimuli via peripheral transducing mechanisms (see Millan, 1999, Prog. Neurobiol., 57, 1-164 for a review). These sensory fibres are known as nociceptors and are characteristically small diameter axons with slow conduction velocities. Nociceptors encode the intensity, duration and quality of noxious stimulus and by virtue of their topographically organised projection to the spinal cord, the location of the stimulus. The nociceptors are found on nociceptive nerve fibres of which there are two main types, A-delta fibres (myelinated) and C fibres (non-myelinated). The activity generated by nociceptor input is transferred, after complex processing in the dorsal horn, either directly, or via brain stem relay nuclei, to the ventrobasal thalamus and then on to the cortex, where the sensation of pain is generated.

Pain may generally be classified as acute or chronic. Acute pain begins suddenly and is short-lived (usually twelve weeks or less). It is usually associated with a specific cause such as a specific injury and is often sharp and severe. It is the kind of pain that can occur after specific injuries resulting from surgery, dental work, a strain or a sprain. Acute pain does not generally result in any persistent psychological response. In contrast, chronic pain is long-term pain, typically persisting for more than three months and leading to significant psychological and emotional problems. Common examples of chronic pain are neuropathic pain (e.g. painful diabetic neuropathy, postherpetic neuralgia), carpal tunnel syndrome, back pain, headache, cancer pain, arthritic pain and chronic post-surgical pain.

When a substantial injury occurs to body tissue, via disease or trauma, the characteristics of nociceptor activation are altered and there is sensitisation in the periphery, locally around the injury and centrally where the nociceptors terminate. These effects lead to a hightened sensation of pain. In acute pain these mechanisms can be useful, in promoting protective behaviours which may better enable repair processes to take place. The normal expectation would be that sensitivity returns to normal once the injury has healed. However, in many chronic pain states, the hypersensitivity far outlasts the healing process and is often due to nervous system injury. This injury often leads to abnormalities in sensory nerve fibres associated with maladaptation and aberrant activity (Woolf & Salter, 2000, Science, 288, 1765-1768).

Clinical pain is present when discomfort and abnormal sensitivity feature among the patient's symptoms. Patients tend to be quite heterogeneous and may present with various pain symptoms. Such symptoms include: 1) spontaneous pain which may be dull, burning, or stabbing; 2) exaggerated pain responses to noxious stimuli (hyperalgesia); and 3) pain produced by normally innocuous stimuli (allodynia—Meyer et al., 1994, Textbook of Pain, 13-44). Although patients suffering from various forms of acute and chronic pain may have similar symptoms, the underlying mechanisms may be different and may, therefore, require different treatment strategies. Pain can also therefore be divided into a number of different subtypes according to differing pathophysiology, including nociceptive, inflammatory and neuropathic pain.

Nociceptive pain is induced by tissue injury or by intense stimuli with the potential to cause injury. Pain afferents are activated by transduction of stimuli by nociceptors at the site of injury and activate neurons in the spinal cord at the level of their termination. This is then relayed up the spinal tracts to the brain where pain is perceived (Meyer et al., 1994, Textbook of Pain, 13-44). The activation of nociceptors activates two types of afferent nerve fibres. Myelinated A-delta fibres transmit rapidly and are responsible for sharp and stabbing pain sensations, whilst unmyelinated C fibres transmit at a slower rate and convey a dull or aching pain. Moderate to severe acute nociceptive pain is a prominent feature of pain from central nervous system trauma, strains/sprains, burns, myocardial infarction and acute pancreatitis, post-operative pain (pain following any type of surgical procedure), post-traumatic pain, renal colic, cancer pain and back pain. Cancer pain may be chronic pain such as tumour related pain (e.g. bone pain, headache, facial pain or visceral pain) or pain associated with cancer therapy (e.g. postchemotherapy syndrome, chronic postsurgical pain syndrome or post radiation syndrome). Cancer pain may also occur in response to chemotherapy, immunotherapy, hormonal therapy or radiotherapy. Back pain may be due to herniated or ruptured intervertabral discs or abnormalities of the lumber facet joints, sacroiliac joints, paraspinal muscles or the posterior longitudinal ligament. Back pain may resolve naturally but in some patients, where it lasts over 12 weeks, it becomes a chronic condition which can be particularly debilitating.

Neuropathic pain is currently defined as pain initiated or caused by a primary lesion or dysfunction in the nervous system. Nerve damage can be caused by trauma and disease and thus the term 'neuropathic pain' encompasses many disorders with diverse aetiologies. These include, but are not limited to, peripheral neuropathy, diabetic neuropathy, post herpetic neuralgia, trigeminal neuralgia, back pain, cancer neuropathy, HIV neuropathy, phantom limb pain, carpal tunnel syndrome, central post-stroke pain and pain associated with chronic alcoholism, hypothyroidism, uremia, multiple sclerosis, spinal cord injury, Parkinson's disease, epilepsy and vitamin deficiency. Neuropathic pain is pathological as it has no protective role. It is often present well after the original cause has dissipated, commonly lasting for years, significantly decreasing a patient's quality of life (Woolf and Mannion, 1999, Lancet, 353, 1959-1964). The symptoms of neuropathic pain are difficult to treat, as they are often heterogeneous even between patients with the same disease (Woolf & Decosterd, 1999, Pain Supp., 6, S141-S147; Woolf and Mannion, 1999, Lancet, 353, 1959-1964). They include spontaneous pain, which can be continuous, and paroxysmal or abnormal evoked pain, such as hyperalgesia (increased sensitivity to a noxious stimulus) and allodynia (sensitivity to a normally innocuous stimulus).

The inflammatory process is a complex series of biochemical and cellular events, activated in response to tissue injury or the presence of foreign substances, which results in swelling and pain (Levine and Taiwo, 1994, Textbook of Pain, 45-56). Arthritic pain is the most common inflammatory pain. Rheumatoid disease is one of the commonest chronic inflammatory conditions in developed countries and rheumatoid arthritis is a common cause of disability. The exact aetiology of rheumatoid arthritis is unknown, but current hypotheses suggest that both genetic and microbiological factors may be important (Grennan & Jayson, 1994, Textbook of Pain, 397-407). It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Houge & Mersfelder, 2002, Ann Pharmacother., 36, 679-686; McCarthy et al., 1994, Textbook of Pain, 387-395). Most patients with osteoarthritis seek medical attention because of the associated pain. Arthritis has a significant impact on psychosocial and physical function and is known to be the leading cause of disability in later life. Ankylosing spondylitis is also a rheumatic disease that causes arthritis of the spine and sacroiliac joints. It varies from intermittent episodes of back pain that occur throughout life to a severe chronic disease that attacks the spine, peripheral joints and other body organs.

Another type of inflammatory pain is visceral pain which includes pain associated with inflammatory bowel disease (IBD). Visceral pain is pain associated with the viscera, which encompass the organs of the abdominal cavity. These organs include the sex organs, spleen and part of the digestive system. Pain associated with the viscera can be divided into digestive visceral pain and non-digestive visceral pain. Commonly encountered gastrointestinal (GI) disorders that cause pain include functional bowel disorder (FBD) and inflammatory bowel disease (IBD). These GI disorders include a wide range of disease states that are currently only moderately controlled, including, in respect of FBD, gastro-esophageal reflux, dyspepsia, irritable bowel syndrome (IBS) and functional abdominal pain syndrome (FAPS), and, in respect of IBD, Crohn's disease, ileitis and ulcerative colitis, all of which regularly produce visceral pain. Other types of visceral pain include the pain associated with dysmenorrhea, cystitis and pancreatitis and pelvic pain.

It should be noted that some types of pain have multiple aetiologies and thus can be classified in more than one area, e.g. back pain and cancer pain have both nociceptive and neuropathic components.

Other types of pain include:
pain resulting from musculo-skeletal disorders, including myalgia, fibromyalgia, spondylitis, sero-negative (non-rheumatoid) arthropathies, non-articular rheumatism, dystrophinopathy, glycogenolysis, polymyositis and pyomyositis;
heart and vascular pain, including pain caused by angina, myocardical infarction, mitral stenosis, pericarditis, Raynaud's phenomenon, scleredoma and skeletal muscle ischemia;
head pain, such as migraine (including migraine with aura and migraine without aura), cluster headache, tension-type headache mixed headache and headache associated with vascular disorders; and
orofacial pain, including dental pain, otic pain, burning mouth syndrome and temporomandibular myofascial pain.
The N-[({2-[4-(2-Ethyl-4,6-dimethyl-1H-imidazo[4,5-c]pyridin-1-yl)phenyl]ethyl}amino)carbonyl]-4-methylbenzenesulfonamide Polymorph Forms of the present invention may also be useful for the treatment of a disorder or condition selected from the group consisting of pain, fever or inflammation associated with rheumatic fever, influenza or other viral infections, common cold, low back and neck pain, skeletal pain, post-partum pain, dysmenorrhea, headache, migraine, toothache, sprains and strains, myositis, neuralgia, fibromyalgia, synovitis, arthritis, including rheumatoid arthritis, degenerative joint diseases (osteoarthritis), gout and ankylosing spondylitis, bursitits, burns including radiation and corrosive chemical injuries, sunburns, pain following surgical and dental procedures or bone fracture, immune and autoimmune diseases such as systemic lupus erythematosus; AIDS (acquired immuno deficiency syndrome), gastrointestinal cancers such as colon cancer; cellular neoplastic transformations or metastic tumor growth; diabetic retinopathy, tumor angiogenesis; prostanoid-induced smooth muscle contraction associated with dysmenorrhea, premature labor, allergic rhinitis, atopic dermatitis, asthma or eosinophil related disorders, hyperimmunoglobulinaemia, Castleman's disease, myeloma; Alzheimer's disease, sleep disorders, endocrine disturbance; glaucoma; bone loss; osteoporosis; promotion of bone formation; Paget's disease: cytoprotection in peptic ulcers, gastritis, regional enteritis, ulcerative colitis, diverticulitis or other gastrointestinal lesions; GI bleeding and patients undergoing chemotherapy; coagulation disorders selected from hypoprothrombinemia, haemophilia and other bleeding problems; kidney disease; thrombosis; occlusive vascular disease; presurgery; and anti-coagulation.
The N-[({2-[4-(2-Ethyl-4,6-dimethyl-1H-imidazo[4,5-c]pyridin-1-yl)phenyl]ethyl}amino)carbonyl]-4-methylbenzenesulfonamide Polymorph Forms of the present invention are also useful in the treatment of IL-6 involved diseases selected from the group consisting of alcoholic cirrhosis, amyloidosis, atherosclerosis, cardiac disease such as angina pectoris, myocardial infarction, myocardiopathy and myocarditis, sclerosis such as multiple sclerosis, and organ transplantation reactions.

Synthetic routes for the preparation of N-[({2-[4-(2-Ethyl-4,6-dimethyl-1H-imidazo[4,5-c]pyridin-1-yl)phenyl]ethyl}amino)carbonyl]-4-methylbenzenesulfonamide are described in WO-A-02/32900 and in the Example Section below.

N-[({2-[4-(2-Ethyl-4,6-dimethyl-1H-imidazo[4,5-c]pyridin-1-yl)phenyl]ethyl}amino)carbonyl]-4-methylbenzenesulfonamide Polymorph Form A may be prepared by crystallisation from a solution of N-[({2-[4-(2-Ethyl-4,6-dimethyl-1H-imidazo[4,5-c]pyridin-1-yl)phenyl]ethyl}amino)carbonyl]-4-methylbenzenesulfonamide in ethyl acetate.

Alternatively, N-[({2-[4-(2-Ethyl-4,6-dimethyl-1H-imidazo[4,5-c]pyridin-1-yl)phenyl]ethyl}amino)carbonyl]-4-methylbenzenesulfonamide Polymorph Form A may be prepared by crystallisation from a solution of N-[({2-[4-(2-Ethyl-4,6-dimethyl-1H-imidazo[4,5-c]pyridin-1-yl)phenyl]ethyl}amino)carbonyl]-4-methylbenzenesulfonamide in acetone.

Alternatively, N-[({2-[4-(2-Ethyl-4,6-dimethyl-1H-imidazo[4,5-c]pyridin-1-yl)phenyl]ethyl}amino)carbonyl]-4-methylbenzenesulfonamide Polymorph Form A may be prepared by crystallisation from a solution of Polymorph Form B in a mixture of acetonitrile and ethyl acetate.

Alternatively, N-[({2-[4-(2-Ethyl-4,6-dimethyl-1H-imidazo[4,5-c]pyridin-1-yl)phenyl]ethyl}amino)carbonyl]-4-methylbenzenesulfonamide Polymorph Form A may be prepared by crystallisation from a solution of Polymorph Form B in a mixture of dichloromethane and acetone by using a seeding crystal of Polymorph Form A.

Alternatively, N-[({2-[4-(2-Ethyl-4,6-dimethyl-1H-imidazo[4,5-c]pyridin-1-yl)phenyl]ethyl}amino)carbonyl]-4-methylbenzenesulfonamide Polymorph Form A may be prepared by crystallisation from a solution of Polymorph Form B in ethanol.

N-[({2-[4-(2-Ethyl-4,6-dimethyl-1H-imidazo[4,5-c]pyridin-1-yl)phenyl]ethyl}amino)carbonyl]-4-methylbenzenesulfonamide Polymorph Form B may be prepared by crystallisation from a solution of N-[({2-[4-(2-Ethyl-4,6-dimethyl-1H-imidazo[4,5-c]pyridin-1-yl)phenyl]ethyl}amino)carbonyl]-4-methylbenzenesulfonamide in dichloromethane and acetone.

Alternatively, N-[({2-[4-(2-Ethyl-4,6-dimethyl-1H-imidazo[4,5-c]pyridin-1-yl)phenyl]ethyl}amino)carbonyl]-4-methylbenzenesulfonamide Polymorph Form B may be prepared by crystallisation from a solution of N-[({2-[4-(2-Ethyl-4,6-dimethyl-1H-imidazo[4,5-c]pyridin-1-yl)phenyl]ethyl}amino)carbonyl]-4-methylbenzenesulfonamide in dichloromethane by partial displacement of the dichloromethane with acetone.

The N-[({2-[4-(2-Ethyl-4,6-dimethyl-1H-imidazo[4,5-c]pyridin-1-yl)phenyl]ethyl}amino)carbonyl]-4-methylbenzenesulfonamide Polymorph Forms of the present invention can be administered alone or in combination with one or more other drugs (or as any combination thereof). Generally, they will be administered as a formulation in association with one or more pharmaceutically acceptable excipients. The term 'excipient' is used herein to describe any ingredient other than the compound(s) of the invention. The choice of excipient will to a large extent depend on factors such as the particular mode of administration, the effect of the excipient on solubility and stability, and the nature of the dosage form.

Thus, as a further aspect of the present invention, there is provided a pharmaceutical composition including N-[({2-[4-(2-Ethyl-4,6-dimethyl-1H-imidazo[4,5-c]pyridin-1-yl)phenyl]ethyl}amino)carbonyl]-4-methylbenzenesulfonamide Polymorph Form A or B and one or more suitable excipients. The composition is suitable for the treatment of pain, inflammation, osteoarthritis or rheumatoid arthritis.

For the avoidance of doubt, references herein to "treatment" include references to curative, palliative and prophylactic treatment.

For non-human animal administration, the term 'pharmaceutical' as used herein may be replaced by 'veterinary.'

Pharmaceutical compositions suitable for the delivery of the Polymorph Forms of the invention and methods for their preparation will be readily apparent to those skilled in the art. Such compositions and methods for their preparation may be found, for example, in *Remington's Pharmaceutical Sciences,* 19th Edition (Mack Publishing Company, 1995).

Oral Administration

The Polymorph Forms of the invention may be administered orally. Oral administration may involve swallowing, so that the compound enters the gastrointestinal tract, and/or buccal, lingual, or sublingual administration by which the compound enters the blood stream directly from the mouth.

Formulations suitable for oral administration include solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccal/mucoadhesive patches.

Liquid formulations include suspensions, solutions, syrups and elixirs. Such formulations may be employed as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The Polymorph Forms of the invention may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in *Pharmaceutical Dosage Forms: Tablets, Vol.* 1, by H. Lieberman and L. Lachman (Marcel Dekker, New York, 1980).

Consumable oral films for human or veterinary use are typically pliable water-soluble or water-swellable thin film dosage forms which may be rapidly dissolving or mucoadhesive and typically comprise a Polymorph Form in accordance with the invention, a film-forming polymer, a binder, a solvent, a humectant, a plasticiser, a stabiliser or emulsifier, a viscosity-modifying agent and a solvent. Some components of the formulation may perform more than one function.

The Polymorph Forms of the invention may be water-soluble or insoluble. A water-soluble compound typically comprises from 1 weight % to 80 weight %, more typically from 20 weight % to 50 weight %, of the solutes. Less soluble compounds may comprise a greater proportion of the composition, typically up to 88 weight % of the solutes. Alternatively, the Polymorph Forms of the invention may be in the form of multiparticulate beads.

The film-forming polymer may be selected from natural polysaccharides, proteins, or synthetic hydrocolloids and is typically present in the range 0.01 to 99 weight %, more typically in the range 30 to 80 weight %.

Other possible ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in *Pharmaceutical Technology On-line,* 25(2), 1-14, by Verma et al (2001). The use of chewing gum to achieve controlled release is described in WO 00/35298.

Parenteral Administration

The Polymorph Forms of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular, intrasynovial and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

Formulations for parenteral administration may be formulated to be immediate and/or modified release. Modified release formulations include delayed-, sustained-, pulsed-, controlled-, targeted and programmed release. Thus the Polymorph Forms of the invention may be formulated as a suspension or as a solid, semi-solid, or thixotropic liquid for administration as an implanted depot providing modified release of the active compound. Examples of such formulations include drug-coated stents and semi-solids and suspensions comprising drug-loaded poly(dl-lactic-coglycolic)acid (PGLA) microspheres.

Topical Administration

The Polymorph Forms of the invention may also be administered topically, (intra)dermally, or transdermally to the skin or mucosa. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958, by Finnin and Morgan (October 1999).

Other means of topical administration include delivery by electroporation, iontophoresis, phonophoresis, sonophoresis and microneedle or needle-free (e.g. Powderject™, Bioject™, etc.) injection. Topical administration may also be achieved using a patch, such as a transdermal iontophoretic patch.

Formulations for topical administration may be formulated to be immediate and/or modified release. Modified release formulations include delayed-, sustained-, pulsed-, controlled-, targeted and programmed release.

The Polymorph Forms of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler, as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane, or as nasal drops. For intranasal use, the powder may comprise a bioadhesive agent, for example, chitosan or cyclodextrin.

The pressurised container, pump, spray, atomizer, or nebuliser contains a solution or suspension of a Polymorph Form in accordance with the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 μg to 20 mg of the compound of the invention per actuation and the actuation volume may vary from 1 μl to 100 μl. A typical formulation may comprise a Polymorph Form in accordance with the invention, propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, PGLA. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from 1 μg to 20 mg of the compound of formula I. The overall daily dose will typically be in the range 1 μg to 100 mg which may be administered in a single dose or, more usually, as divided doses throughout the day.

Rectal/Intravaginal Administration

The Polymorph Forms of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

Ocular/Aural Administration

The Polymorph Forms of the invention may also be administered directly to the eye or ear, typically in the form of drops of a micronised suspension or solution in isotonic, pH-adjusted, sterile saline. Other formulations suitable for ocular and aural administration include ointments, gels, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

Other Technologies

The Polymorph Forms of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

Kit-of-Parts

Inasmuch as it may desirable to administer a combination of active compounds, for example, for the purpose of treating a particular disease or condition, it is within the scope of the present invention that two or more pharmaceutical compositions, at least one of which contains a Polymorph Form in accordance with the invention, may conveniently be combined in the form of a kit suitable for coadministration of the compositions.

Thus the kit of the invention comprises two or more separate pharmaceutical compositions, at least one of which contains a Polymorph Form in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

Dosage

For administration to human patients, the total daily dose of the Polymorph Forms of the invention is typically in the range 0.1 mg to 3000 mg depending, of course, on the mode of administration. For example, oral administration may require a total daily dose of from 1 mg to 3000 mg, while an intravenous dose may only require from 0.1 mg to 300 mg. The total-daily dose may be administered in single or divided doses and may, at the physician's discretion, fall outside of the typical range given herein. Preferably the total daily dose is in the range 0.1 mg to 500 mg.

These dosages are based on an average human subject having a weight of about 60 kg to 70 kg. The physician will readily be able to determine doses for subjects whose weight falls outside this range, such as infants and the elderly.

For the avoidance of doubt, references herein to "treatment" include references to curative, palliative and prophylactic treatment.

The Polymorph Forms of the present invention may also optionally be combined with another pharmacologically active compound, or with two or more other pharmacologically active compounds, particularly for the treatment of pain. For example, the Polymorph Forms of the present invention, as defined above, may be administered simultaneously, sequentially or separately in combination with one or more agents selected from:

- an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;
- a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;
- a barbiturate sedative, e.g. amobarbital, aprobarbital, butabarbital, butabital, mephobarbital, metharbital, methohexital, pentobarbital, phenobartital, secobarbital, talbutal, theamylal or thiopental;
- a benzodiazepine having a sedative action, e.g. chlordiazepoxide, clorazepate, diazepam, flurazepam, lorazepam, oxazepam, temazepam or triazolam;
- an $H_1$ antagonist having a sedative action, e.g. diphenhydramine, pyrilamine, promethazine, chlorpheniramine or chlorcyclizine;
- a sedative such as glutethimide, meprobamate, methaqualone or dichloralphenazone;
- a skeletal muscle relaxant, e.g. baclofen, carisoprodol, chlorzoxazone, cyclobenzaprine, methocarbamol or orphrenadine;
- an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex®, a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2(1H)-quinolinone;
- an alpha-adrenergic, e.g. doxazosin, tamsulosin, clonidine, guanfacine, dexmetatomidine, modafinil, or 4-amino-6,7-dimethoxy-2-(5-methane-sulfonamido-1,2,3,4-tetrahydroisoquinol-2-yl)-5-(2-pyridyl) quinazoline;
- a tricyclic antidepressant, e.g. desipramine, imipramine, amitriptyline or nortriptyline;
- an anticonvulsant, e.g. carbamazepine, lamotrigine, topiratmate or valproate;
- a tachykinin (NK) antagonist, particularly an NK-3, NK-2 or NK-1 antagonist, e.g. (αR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);
- a muscarinic antagonist, e.g oxybutynin, tolterodine, propiverine, tropsium chloride, darifenacin, solifenacin, temiverine and ipratropium;
- a COX-2 selective inhibitor, e.g. celecoxib, rofecoxib, parecoxib, valdecoxib, deracoxib, etoricoxib, or lumiracoxib;
- a coal-tar analgesic, in particular paracetamol;
- a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion® or sarizotan;
- a vanilloid receptor agonist (e.g. resinferatoxin) or antagonist (e.g. capsazepine);
- a beta-adrenergic such as propranolol;
- a local anaesthetic such as mexiletine;
- a corticosteroid such as dexamethasone;
- a 5-HT receptor agonist or antagonist, particularly a $5\text{-}HT_{1B/1D}$ agonist such as eletriptan, sumatriptan, naratriptan, zolmitriptan or rizatriptan;
- a $5\text{-}HT_{2A}$ receptor antagonist such as R(+)-alpha-(2,3-dimethoxy-phenyl)-1-[2-(4-fluorophenylethyl)]-4-piperidinemethanol (MDL-100907);
- a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;
- Tramadol®;
- a PDEV inhibitor, such as 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazino[2',1':6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl)pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;
- an alpha-2-delta ligand such as gabapentin, pregabalin, 3-methylgabapentin, (1α,3α,5α) (3-amino-methyl-bicyclo[3.2.0]hept-3-yl)-acetic acid, (3S,5R)-3-aminomethyl-5-methyl-heptanoic acid, (3S,5R)-3-amino-5-methyl-heptanoic acid, (3S,5R)-3-amino-5-methyloctanoic acid, (2S,4S)-4-(3-chlorophenoxy)proline, (2S,4S)-4-(3-fluorobenzyl)-proline, [(1R,5R,6S)-6-(aminomethyl)bicyclo[3.2.0]hept-6-yl]acetic acid, 3-(17 aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3-aminomethyl-5-methyl-octanoic acid, (3S,5R)-3-amino-5-methyl-nonanoic acid, (3S,5R)-3-amino-5-methyl-octanoic acid, (3R,4R,5R)-3-amino-4,5-dimethyl-heptanoic acid and (3R,4R,5R)-3-amino-4,5-dimethyl-octanoic acid;

a cannabinoid;

metabotropic glutamate subtype 1 receptor (mGluR1) antagonist;

a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;

a noradrenaline (norepinephrine) reuptake inhibitor, such as maprotiline, lofepramine, mirtazepine, oxaprotiline, fezolamine, tomoxetine, mianserin, buproprion, buprorion metabolite hydroxybuproprion, nomifensine and viloxazine (Vivalan®), especially a selective noradrenaline reuptake inhibitor such as reboxetine, in particular (S,S)-reboxetine;

a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran and imipramine;

an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl)amino]-5-heptenoic acid, 2-[[(1R,3S)-3-amino-4-hydroxy-1-(5-thiazolyl)-butyl]thio]-5-chloro-3-pyridinecarbonitrile; 2-[[(1R,3S)-3-amino-4-hydroxy-1-(5-thiazolyl)butyl]thio]-4-chlorobenzonitrile, (2S,4R)-2-amino-4-[[2-chloro-5-(trifluoromethyl)phenyl]thio]-5-thiazolebutanol, 2-[[(1R,3S)-3-amino-4-hydroxy-1-(5-thiazolyl)butyl]thio]-6-(trifluoromethyl)-3 pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino)ethyl]phenyl]thiophene-2-carboxamidine, or guanidinoethyldisulfide;

an acetylcholinesterase inhibitor such as donepezil;

a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870, a 5-lipoxygenase inhibitor, such as zileuton, 6-[(3-fluoro-5-[4-methoxy-3,4,5,6-tetrahydro-2H-pyran-4-yl])phenoxy-methyl]-1-methyl-2-quinolone (ZD-2138), or 2,3,5-trimethyl-6-(3-pyridylmethyl), 1,4-benzoquinone (CV-6504);

a sodium channel blocker, such as lidocaine;

a 5-HT3 antagonist, such as ondansetron;

and the pharmaceutically acceptable salts and solvates thereof.

The present invention extends to a combination comprising N-[({2-[4-(2-Ethyl-4,6-dimethyl-1H-imidazo[4,5-c]pyridin-1-yl)phenyl]ethyl}amino)carbonyl]-4-methylbenzenesulfonamide Polymorph Form A or B and one or more therapeutic agents, such as those listed above, for simultaneous, separate or sequential use in the curative, prophylactic or palliative treatment of pain, inflammation, osteoarthritis or rheumatoid arthritis.

Thus, the invention provides:
I. Essentially pure, crystalline, N-[({2-[4-(2-Ethyl-4,6-dimethyl-1H-imidazo[4,5-c]pyridin-1-yl)phenyl]ethyl}amino)carbonyl]-4-methylbenzenesulfonamide Polymorph Forms A and B;
II. Processes for the preparation of essentially pure, crystalline, N-[({2-[4-(2-Ethyl-4,6-dimethyl-1H-imidazo[4,5-c]pyridin-1-yl)phenyl]ethyl}amino)carbonyl]-4-methylbenzenesulfonamide Polymorph Forms A and B;
III. A pharmaceutical composition including essentially pure, crystalline, N-[({2-[4-(2-Ethyl-4,6-dimethyl-1H-imidazo[4,5-c]pyridin-1-yl)phenyl]ethyl}amino)carbonyl]-4-methylbenzenesulfonamide Polymorph Forms A or B and one or more pharmaceutically acceptable excipients;
IV. Essentially pure, crystalline, N-[({2-[4-(2-Ethyl-4,6-dimethyl-1H-imidazo[4,5-c]pyridin-1-yl)phenyl]ethyl}amino)carbonyl]-4-methylbenzenesulfonamide Polymorph Forms A and B for use as a medicament;
V. The use of essentially pure, crystalline, N-[({2-[4-(2-Ethyl-4,6-dimethyl-1H-imidazo[4,5-c]pyridin-1-yl)phenyl]ethyl}amino)carbonyl]-4-methylbenzenesulfonamide Polymorph Forms A or B in the manufacture of a medicament for the treatment of pain, inflammation, osteoarthritis or rheumatoid arthritis;
VI. A method of treating pain, inflammation, osteoarthritis or rheumatoid arthritis which includes administering an effective amount of essentially pure, crystalline, N-[({2-[4-(2-Ethyl-4,6-dimethyl-1H-imidazo[4,5-c]pyridin-1-yl)phenyl]ethyl}amino)carbonyl]-4-methylbenzenesulfonamide Polymorph Forms A or B, or a pharmaceutically acceptable composition thereof, to an animal, including an human, in need of such treatment.

EXAMPLES

The following example is for reference only.

Example 1

2-ETHYL-5,7-DIMETHYL-3-(4-{2-[({[(4-METHYLPHENYL)SULFONYL]AMINO}CARBONYL)AMINO]ETHYL}PHENYL)-3H-IMIDAZO[4,5-b]PYRIDINE

STEP 1. 4,6-Dimethyl-3-nitro-2(1H)-pyridinone

A mixture of ethyl nitroacetate (80.0 g, 601 mmol) in ammonium hydroxide (25% $NH_3$ in water, 400 mL) was stirred at room temperature for 3 days, and then the solution was concentrated by air-drying. The residue was dissolved in water (450 mL). To the solution was added 2,4-pentanedione (73.1 g, 730 mmol), pyridine (16.2 mL, 200 mmol) and acetic acid (11.4 mL, 200 mmol), and the mixture was stirred for an additional 7 days. The resulting precipitates were collected by filtration and dried under reduced pressure to give 35.0 g (35%) of the title compound as yellow solids: $^1$H-NMR (DMSO-$d_6$) δ 12.44 (1H, br. s), 6.06 (1H, s), 2.19 (3H, s), 2.13 (3H, s).

STEP 2. 2-Chloro-4,6-dimethyl-3-nitropyridine

A mixture of 4,6-dimethyl-3-nitro-2(1H-pyridinone (step 1, 10.0 g, 29.7 mmol) in phosphorus oxychloride (35 mL, 187.3 mmol) was stirred at 95° C. for 3 h, then cooled to 45° C. The excess amount of phosphorus oxychloride was removed by distillation under reduced pressure at 45° C. The residue was cooled to room temperature, and diluted with dichloromethane (75 mL). The resulting solution was cooled to 0° C., and 2N hydrochloric acid (50 mL) was added dropwise into the solution. The organic layer was separated, and washed with 2N hydrochloric acid (4×25 mL), 2N aqueous NaOH (2×50 mL) and brine (50 mL). The organic phase was dried (MgSO$_4$) and concentrated under reduced pressure to give 10.0 g (90%) of the title compound as white solids: $^1$H-NMR (CDCl$_3$) δ 7.07 (1H, s), 2.56 (3H, s), 2.35 (3H, s).

STEP 3. 2-{4-[(4,6-Dimethyl-3-nitro-2-pyridinyl) amino]phenyl}ethanol

A mixture of 2-chloro-4,6-dimethyl-3-nitropyridine (step 2, 1.3 g, 7.0 mmol) and 4-aminophenylethyl alcohol (1.4 g, 10.2 mmol) was placed in a sealed tube and heated at 150° C. for 3 h. The reaction mixture was cooled and purified by flash column chromatography on silica gel eluting with hexane/ethyl acetate (2:1) to afford 1.6 g (80%) of the title compound as orange solids: $^1$H-NMR (CDCl$_3$) δ 9.55 (1H, br. s), 7.57 (2H, d, J=8.4 Hz), 7.20 (2H, d, J=8.4 Hz), 6.52 (1H, s), 3.84 (2H, t, J=6.4 Hz), 2.85 (2H, t, J=6.4 Hz), 2.54 (3H, s), 2.42 (3H, s).

STEP 4. 2-{4-[(3-Amino-4,6-dimethyl-2-pyridinyl) amino]phenyl}ethanol

To a stirred solution of 2-{4-[(4,6-dimethyl-3-nitro-2-pyridinyl)amino]phenyl}ethanol (step 3, 1.6 g, 5.6 mmol) in ethyl acetate (15 mL) was added 10% Pd—C (160 mg). The mixture was stirred at room temperature for 6 h under hydrogen atmosphere. The palladium catalyst was removed by filtration and washed with ethanol (100 mL). The filtrate was concentrated under reduced pressure to afford 1.3 g (92%) of the title compound as pale yellow solids: $^1$H-NMR (CDCl$_3$) δ 7.10 (4H, s), 6.61 (1H, s), 3.81 (2H, t, J=6.4 Hz), 2.80 (2H, t, J=6.4 Hz), 2.36 (3H, s), 2.19 (3H, s).

STEP 5. 2-[4-(2-Ethyl-5,7-dimethyl-3H-imidazo[4,5-b]pyridin-3-yl)phenyl]ethyl propionate To a stirred suspension of 2-{4-[(3-amino-4,6-dimethyl-2-pyridinyl)amino]phenyl}ethanol (step 4, 1.3 g, 5.1 mmol) in toluene (30 mL) was added dropwise propionyl chloride (990 mg, 10.7 mmol) at 0° C., and the reaction mixture was heated at reflux temperature for 2 h. After cooling, the mixture was poured into water (50 mL) and extracted with ethyl acetate (100 mL). The organic layer was washed with 2N aqueous NaOH (50 mL) and brine (50 mL), then dried (MgSO$_4$). Removal of solvent gave 1.8 g (quant.) of the title compound as brown solids: $^1$H-NMR (CDCl$_3$) δ 7.41 (2H, d, J=8.4 Hz), 7.33 (2H, d, J=8.4 Hz), 6.90 (1H, s), 4.37 (2H, t, J=6.9 Hz), 3.04 (2H, t, J=6.9 Hz), 2.82 (2H, q, J=7.6 Hz), 2.65 (3H, s), 2.52 (3H, s), 2.35 (2H, q, J=7.6 Hz), 1.27 (3H, t, J=7.6 Hz), 1.14 (3H, t, J=7.6 Hz).

STEP 6. 2-[4-(2-Ethyl-5,7-dimethyl-3H-imidazo[4,5-b]pyridin-3-yl)phenyl]ethanol To a solution of 2-[4-(2-ethyl-5,7-dimethyl-3H-imidazo[4,5-b]pyridin-3-yl)phenyl]ethyl propionate (step 5, 1.75 g, 5.1 mmol) in methanol/THF (v/v, 1:1, 28 mL) was added 4N aqueous LiOH (4.6 mL, 18.4 mmol) and the resulting mixture was stirred at room temperature. After 3 h, the mixture was concentrated.

The residue was dissolved in water (30 mL) and extracted with ethyl acetate (100 mL). The organic layer was washed with brine (50 mL), dried (MgSO$_4$), and concentrated. Purification by flash column chromatography on silica gel eluting with hexane/ethyl acetate (gradient elution from 2:1 to 0:1) to afford 1.3 g (86%) of the title compound as pale brown solids: $^1$H-NMR (CDCl$_3$) δ 7.40 (2H, d, J=8.4 Hz), 7.31 (2H, d, J=8.4 Hz), 6.91 (1H, s), 3.81-3.75 (2H, m), 3.47 (1H, br. s), 2.92 (2H, t, J=6.9 Hz), 2.81 (2H, q, J=7.6 Hz), 2.66 (3H, s), 2.51 (3H, s), 1.27 (3H, t, J=7.6 Hz).

STEP 7. 3-[4-(2-Chloroethyl)phenyl]-2-ethyl-5,7-dimethyl-3H-imidazo[4,5-b]pyridine To a solution of 2-[4-(2-ethyl-5,7-dimethyl-3H-imidazo[4,5-b]pyridin-3-yl)phenyl]ethanol (step 6, 2.2 g, 7.4 mmol) in toluene (40 mL) was added thionyl chloride (2.0 mL, 23.6 mmol), and the resulting mixture was stirred at 80° C. for 3 h. The volatile components were removed under reduced pressure, and the residue was purified by flash column chromatography on silica gel eluting with hexane/ethyl acetate (gradient elution from 2:1 to 1:1) to afford 2.1 g (90%) of the title compound as white solids: $^1$H-NMR (CDCl$_3$) δ 7.41 (2H, d, J=8.4 Hz), 7.35 (2H, d, J=8.4 Hz), 6.90 (1H, s), 3.78 (2H, t, J=7.4 Hz), 3.15 (2H, t, J=7.4 Hz), 2.83 (2H, q, J=7.6 Hz), 2.71 (3H, s), 2.54 (3H, s), 1.28 (3H, t, J=7.6 Hz).

STEP 8. 2-[4-(2-Ethyl-5,7-dimethyl-3H-imidazo[4,5-b]pyridin-3-yl)phenyl]ethyl azide To a stirred solution of 3-[4-(2-chloroethyl)phenyl]-2-ethyl-5,7-dimethyl-3H-imidazo[4,5-b]pyridine (step 7, 2.8 g, 9.0 mmol) and KI (1.5 g, 9.0 mmol) in DMF (50 mL) was added sodium azide (1.2 g, 18.0 mmol), and then the resulting mixture was stirred overnight at 100° C. The reaction mixture was poured into water (100 mL), and extracted with ethyl acetate (100 mL). The organic layer was washed with water (50 mL) and brine (50 mL), then dried (Na$_2$SO$_4$). After removal of solvent, the crude product was purified by flash column chromatography on silica gel eluting with hexane/ethyl acetate (1:1) to afford 2.35 g (85%) of the title compound as white solids: $^1$H-NMR (CDCl$_3$) δ 7.41 (2H, d, J=8.4 Hz), 7.35 (2H, d, J=8.4 Hz), 6.90 (1H, s), 3.59 (2H, t, J=7.1 Hz), 2.99 (2H, t, J=7.1 Hz), 2.83 (2H, q, J=7.6 Hz), 2.65 (3H, s), 2.52 (3H, s), 1.27 (3H, t, J=7.6 Hz).

STEP 9. 2-[4-(2-Ethyl-5,7-dimethyl-3H-imidazo[4,5-b]pyridin-3-yl)phenyl]ethylamine To a solution of 2-[4-(2-ethyl-5,7-dimethyl-3H-imidazo[4,5-b]pyridin-3-yl)phenyl]ethyl azide (step 8, 2.35 g, 7.3 mmol) in methanol (50 mL) was added 10% Pd—C (200 mg). The resulting mixture was stirred for 4 h under hydrogen atmosphere. The mixture was filtered through a pad of Celite and the filtrate was concentrated. The residue was purified by flash column chromatography on silica gel eluting with dichloromethane/methanol/triethylamine (100:5:1) to afford 2.01 g (94%) of the title compound as white solids: $^1$H-NMR (CDCl$_3$) δ 7.39 (2H, d, J=8.4 Hz), 7.32 (2H, d, J=8.4 Hz), 6.90

(1H, s), 3.05 (2H, t, J=7.3 Hz), 2.88-2.78 (4H, m), 2.65 (3H, s), 2.51 (3H, s), 1.28 (3H, t, J=7.6 Hz).

STEP 10. 2-Ethyl-5,7-dimethyl-3-(4-[2-[({[(4-methylphenyl)sulfonyl]amino]carbonyl)amino]ethyl}phenyl)-3H-imidazo[4,5-b]pyridine

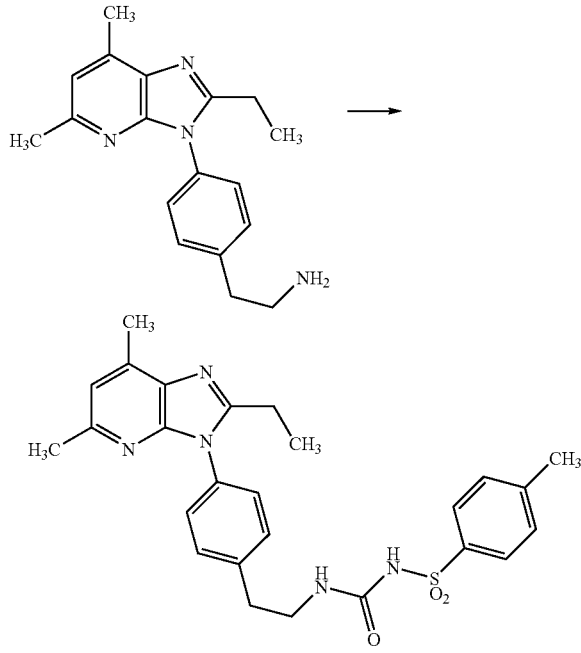

To a solution of 2-[4-(2-ethyl-5,7-dimethyl-3H-imidazo[4,5-b]pyridin-3-yl)phenyl]ethylamine (step 9, 1.2 g, 4.0 mmol) in dichloromethane (15 mL) was added p-toluenesulfonyl isocyanate (805 mg, 4.0 mmol). The resulting mixture was stirred at room temperature for 3 h. After removal of solvent, the residue was purified by flash column chromatography on silica gel eluting with dichloromethane/methanol (20:1) to afford 1.10 g (56%) of the title compound as white solids: ¹H-NMR (CDCl₃) δ 7.85 (2H, d, J=8.2 Hz), 7.32 (2H, d, J=8.2 Hz), 7.23 (2H, d, J=8.4 Hz), 7.16 (2H, d, J=8.4 Hz), 6.91 (1H, s), 6.12 (1H, br. s), 3.55-3.46 (2H, m), 2.85 (2H, t, J=6.3 Hz), 2.74-2.64 (5H, m), 2.42 (3H, s), 2.41 (3H, s), 1.21 (3H, t, J=7.6 Hz).

The following Example illustrates the previously known method of preparing N-[({2-[4-(2-Ethyl-4,6-dimethyl-1H-imidazo[4,5-c]pyridin-1-yl)phenyl]ethyl}amino)carbonyl]-4-methylbenzenesulfonamide, as described in WO-A-02/32900.

Example 2

2-ETHYL-4,6-DI METHYL-1-(4-{2-[({[(4-METHYLPHENYL)SULFONYL]AMINO}CARBONYL)AMINO]ETHYL}PHENYL)-1H-IMIDAZO[4,5-c]PYRIDINE

STEP 1. 2-[4-[(2,6-Dimethyl-3-nitro-4-pyridinyl)amino]phenyl]ethanol

The title compound was prepared according to the procedure described in step 3 of Example 1 from 4-chloro-2,6-dimethyl-3-nitropyridine (Tanaka, A.; et al. *J. Med. Chem.*, 1999, 41, 4408.) and 4-aminophenylethyl alcohol.
¹H-NMR (CDCl₃) δ 8.74 (1H, br. s), 7.31 (2H, d, J=8.2 Hz), 7.18 (2H, d, J=8.2 Hz), 6.68 (1H, s), 3.95-3.89 (2H, m), 2.91 (2H, t, J=6.6 Hz), 2.72 (3H, s), 2.36 (3H, s).

STEP 2. 2-{4-[(3-Amino-2,6-dimethyl-4-pyridinyl)amino]phenyl}ethanol

The title compound was prepared according to the procedure described in step 4 of Example 1 from 2-{4-[(2,6-dimethyl-3-nitro-4-pyridinyl)amino]phenyl}ethanol (step 1).
¹H-NMR (CDCl₃) δ 7.19 (2H, d, J=8.4 Hz), 7.01 (2H, d, J=8.6 Hz), 6.76 (1H, s), 5.82 (1H, br. s), 3.87 (2H, t, J=6.4 Hz), 3.18 (2H, br. s), 2.85 (2H, t, J=6.4 Hz), 2.44 (3H, s), 2.35 (3H, s).

STEP 3. 2-[4-(2-Ethyl-4,6-dimethyl-1H-imidazo[4,5-c]pyridin-1-yl)phenyl]ethyl propionate A mixture of 2-{4-[(3-amino-2,6-dimethyl-4-pyridinyl)amino]phenyl}ethanol (step 2, 2.4 g, 9.3 mmol), propionic anhydride (13 mL, 101 mmol) and propionic acid (13 mL, 174 mmol) was stirred at 120° C. for 16 h. After cooling, the mixture was diluted with 2N aqueous NaOH (150 mL) and extracted with dichloromethane (3×150 mL). The combined organic extracts were washed with brine (50 mL), dried (MgSO₄), and concentrated. Purification by flash column chromatography on silica gel eluting with dichloromethane/methanol (gradient elution from 20:1 to 10:1) afforded 2.3 g (69%) of the title compound as a brown oil: ¹H-NMR (CDCl₃) δ 7.44 (2H, d, J=8.1 Hz), 7.27 (2H, d, J=8.2 Hz), 6.72 (1H, s), 4.38 (2H, t, J=6.9 Hz), 3.07 (2H, t, J=7.1 Hz), 2.88 (3H, s), 2.82 (2H, q, J=7.6 Hz), 2.56 (3H, s), 2.36 (2H, q, J=7.6 Hz), 1.29 (3H, t, J=7.6 Hz), 1.15 (3H, t, J=7.7 Hz).

STEP 4. 2-[4-(2-Ethyl-4,6-dimethyl-1H-imidazo[4,5-c]pyridin-1-yl)phenyl]ethanol

The title compound was prepared according to the procedure described in step 6 of Example 1 from 2-[4-(2-ethyl-4,6-dimethyl-1H-imidazo[4,5-c]pyridin-1-yl)phenyl]ethyl propionate (step 3).
¹H-NMR (CDCl₃) δ 7.46 (2H, d, J=8.1 Hz), 7.26 (2H, d, J=8.1 Hz), 6.73 (1H, s), 4.00 (2H, t, J=6.6 Hz), 3.01 (2H, t, J=6.4 Hz), 2.88 (3H, s), 2.81 (2H, q, J=7.5 Hz), 2.54 (3H, s), 1.29 (3H, t, J=7.5 Hz).

STEP 5. 1-[4-(2-Chloroethyl)phenyl]-2-ethyl-4,6-dimethyl-1H-imidazo[4,5-c]pyridine The title compound was prepared according to the procedure described in step 7 of Example 1 from 2-[4-(2-ethyl-4,6-dimethyl-1H-imidazo[4,5-c]pyridin-1-yl)phenyl]ethanol (step 4).
TLC Rf=0.1 (ethyl acetate).

STEP 6. 1-[4-(2-Azidoethyl)phenyl]-2-ethyl-4,6-dimethyl-1H-imidazo[4,5-c]pyridine The title compound was prepared according to the procedure described in step 8 of Example 1 from 1-[4-(2-chloroethyl)phenyl]-2-ethyl-4,6-dimethyl-1H-imidazo[4,5-c]pyridine (step 5).

$^1$H-NMR (CDCl$_3$) δ 7.46 (2H, d, J=8.0 Hz), 7.29 (2H, d, J=7.7 Hz), 6.72 (1H, s), 3.62 (2H, t, J=6.9 Hz), 3.02 (2H, t, J=6.9 Hz), 2.88 (3H, s), 2.81 (2H, q, J=7.4 Hz), 2.56 (3H, s), 1.29 (3H, t, J=7.6 Hz).

STEP 7. 2-[4-(2-Ethyl-4,6-dimethyl-1H-imidazo[4, 5-c]pyridin-1-yl)phenyl]ethylamine The title compound was prepared according to the procedure described in step 9 of Example 1 from 1-[4-(2-azidoethyl)phenyl]-2-ethyl-4,6-dimethyl-1H-imidazo[4,5-c]pyridine (step 6).
$^1$H-NMR (CDCl$_3$) δ 7.42 (2H, d, J=8.2 Hz), 7.26 (2H, d, J=8.4 Hz), 6.73 (1H, s), 3.08 (2H, t, J=6.9 Hz), 2.90-2.78 (4H, m), 2.88 (3H, s), 2.56 (3H, s), 1.30 (3H, t, J=7.3 Hz).

STEP 8. 2-Ethyl-4,6-dimethyl-1-(4-[2-[({[(4-methylphenyl)sulfonyl]amino]carbonyl)amino]
ethyl}phenyl)-1H-imidazo[4,5-c]pyridine The title compound was prepared according to the procedure described in step 10 of Example 1 from 2-[4-(2-ethyl-4, 6-dimethyl-1H-imidazo[4,5-c]pyridin-1-yl)phenyl]ethylamine (step 7). mp 143° C.; MS (ESI) m/z 492.12 (M+H)$^+$; $^1$H-NMR (CDCl$_3$) δ 7.77 (2H, d, J=8.3 Hz), 7.38 (2H, d, J=8.4 Hz), 7.25 (2H, d, J=8.4 Hz), 7.20 (2H, d, J=8.4 Hz), 6.77 (1H, s), 3.58-3.51 (2H, m), 2.92 (2H, t, J=7.0 Hz), 2.89 (3H, s), 2.79 (2H, q, J=7.5 Hz), 2.53 (3H, s), 2.38 (3H, s), 1.28 (3H, t, J=7.5 Hz).

Example 3

N-[({2-[4-(2-Ethyl-4,6-dimethyl-1H-imidazo[4,5-c] pyridin-1-yl)phenyl]ethyl}amino)carbonyl]-4-methylbenzenesulfonamide Polymorph Form A (alternatively named_2-Ethyl-4,6-dimethyl-1-(4-{2-[({[(4-methylphenyl)sulfonyl]amino}carbonyl)amino] ethyl}phenyl)-1H-imidazo[4,5-c]pyridine)

Step 1: Crude Amorphous Product

In a 20 L, 4-necked round bottom flask equipped with a mechanical stirrer, thermometer, and two 300 mL dropping funnels was immersed in a water bath (water bath temperature; 18° C.). In the flask, to a solution of 508 g of 2-[4-(2-ethyl-4,6-dimethyl-1H-imidazo[4,5-c]pyridin-1-yl)phenyl] ethanamine and 480 mL of triethylamine in 3.5 L of CH$_2$Cl$_2$ was added 270.4 mL of p-tosyl isocyanate dropwise slowly from one of the dropping funnel during the period of 1.0 h maintaining the internal temperature below 28° C. The resulting solution was stirred at room temperature for 1 h, then 6.0 L of 1.0 M aqueous citric acid solution was added dropwise during the period of 30 min maintaining the internal temperature below 22° C. The resulting mixture was stirred vigorously at room temperature for 30 min, then 1.70 L of 2.0 N aqueous NaOH solution was added dropwise. After the completion of the addition, pH value of the solution was confirmed to be 5-5.5. The layers were then separated, and the aqueous layer was re-extracted with 1.0 L of CH$_2$Cl$_2$ and the organic layer was combined. The organic layer was washed with the mixture of 3.0 L of 0.3 M aqueous solution of citric acid and 1.2 L of 2.0 N aqueous NaOH solution. After layers were separated, the aqueous layer was re-extracted with 1.0 L of CH$_2$Cl$_2$ and the organic layer was combined. The resulting organic layer was added 300 g of Na$_2$SO$_4$ and 15.0 g of charcoal, and the mixture was stirred gently at room temperature for 12 h. After the mixture was filtered through celite pad (1 kg), the filtrate was combined with the filtrate of the 70 g scale pilot reaction performed prior to this experiment. The combined filtrate was concentrated to give 1.03 kg of the crude product of a pale yellow amorphous solid.

Step 2: Conversion to, and Purification of, Polymorph Form A

In a 10 L round bottom, 4-necked flask equipped with a mechanical stirrer, thermometer and reflux condenser was immersed in a water bath. In the flask, 5.15 L of hot (40° C.) acetone was added to the crude N-[({2-[4-(2-ethyl-4,6-dimethyl-1H-imidazo[4,5-c]pyridin-1-yl)phenyl]ethyl}amino) carbonyl]-4-methylbenzenesulfonamide (Step 1, 1.03 kg). The mixture was stirred at 50° C. for 7 h under nitrogen atmosphere, then cooled slowly to room temperature during the period of 16 h. 515 mL of acetone was added and the mixture was stirred at room temperature under nitrogen atmosphere for 7 h. The crystals were filtered through paper filter, washed with 515 mL of acetone and dried by flowing nitrogen gas for 15 h to give crystals of the title compound (859 g, 1.75 mol), which were further purified by the following procedure.

In a 10 L stainless 3-necked reactor equipped with a mechanical stirrer, thermometer and reflux condenser was immersed in a water bath. In the flask, a mixture (suspension) of 859 g of the above compound in 1.72 L of acetone was stirred at 50° C. for 8 h, then cooled to room temperature during the period of 14 h. The reaction mixture was stirred at 50° C. for 8 h, then cooled to room temperature during the period of 14 h. Aliquot was taken out and crystals were collected by suction to prepare a sample for the HPLC analysis to determine the purity of the crystal. The mixture was stirred at room temperature under nitrogen atmosphere for 8 h. The crystals were filtered off using a paper filter, washed with 172 mL of acetone, dried by flowing nitrogen gas for 15 h and dried under reduced pressure at 40° C. for 20 h (837 g, 1.70 mol). The product was further purified by the following procedure.

In a 12 L round bottom, 4-necked flask equipped with a mechanical stirrer, thermometer and reflux condenser was immersed in a water bath. In the flask, 3.34 L of acetone was added to the aforementioned crystals (836 g). The mixture was stirred at 50° C. for 4 h under nitrogen atmosphere, then, cooled slowly to room temperature during the period of 15 h. Aliquot was taken out and crystals were collected by suction to prepare a sample for the HPLC analysis to determine the purity of the crystal. The reaction mixture was stirred at 50° C. for 9 h, then, cooled to room temperature during the period of 15 h. Aliquot was taken out and crystals were collected by suction prepare a sample for the HPLC analysis to determine the purity of the crystal. The reaction mixture was stirred at 50° C. for 8 h, and then cooled to room temperature during the period of 64 h. Aliquot was taken out and crystals were collected by suction to prepare a sample for the HPLC analysis to determine the purity of the crystal. The reaction mixture was stirred at 50° C. for 9 h, and then cooled to room temperature during the period of 14 h. Aliquot was taken out and crystals were collected by suction to prepare a sample for the HPLC analysis to determine the purity of the crystal. The mixture was stirred at room temperature under nitrogen atmosphere for 6 h. The crystals were filtered through paper filter, washed with 1.67 L of acetone, dried by flowing nitrogen gas for 22 h, and dried under reduced pressure at 40° C. for 17 h to give the title compound, Polymorph Form A (771 g, 1.57 mol).

Alternatively, Polymorph Form A may be prepared according to the following procedure:

Example 4

N-[([2-[4-(2-Ethyl-4,6-dimethyl-1H-imidazo[4,5-c] pyridin-1-yl)phenyl]ethyl]amino)carbonyl]-4-methylbenzenesulfonamide Polymorph Form A

(alternatively named 2-Ethyl-4,6-dimethyl-1-(4-{2-[({[(4-methylphenyl)sulfonyl]amino}carbonyl)amino] ethyl}phenyl)-1H-imidazo[4,5-c]pyridine)

To a clean and dry 12 L 3-neck round-bottom flask were charged 2-[4-(2-ethyl-4,6-dimethyl-1H-imidazo[4,5-c]pyridin-1-yl)phenyl]ethanamine (422 g, 1.43 moles) and $CH_2Cl_2$ (3.37 L). Tosyl isocyanate (217 mL, 1.43 moles) dissolved in $CH_2Cl_2$ (851 mL) was added to the reaction keeping the temperature below 21° C. and was stirred for at least 90 minutes. The reaction was deemed complete by HPLC and activated charcoal (DARCO KB-B, 4.2 g) was added. The resulting slurry was filtered through a 0.5-micron filter into a speck free 5 L 3-neck round-bottom flask and the filter washed with $CH_2Cl_2$ (421 mL). The reaction was atmospherically concentrated to a minimum stirable volume and displacement continued with speck freed acetone until an internal temperature of 58° C. to 62° C. was achieved and final volume was ~1.3 L. The reaction was cooled to at least 30° C. and seed of N-[({2-[4-(2-Ethyl-4,6-dimethyl-1H-imidazo[4,5-c]pyridin-1-yl)phenyl]ethyl}amino)carbonyl]-4-methylbenzenesulfonamide Polymorph Form A was added. The reaction was allowed to granulate between 20° C. and 25° C. for at least 10 hours. After cooling reaction to 0° C. to 5° C. and granulating for at least 2 hours, the reaction was filtered on a speck free filter. The solids were washed two times with speck free acetone (1.68 L) cooled to 0° C. to 5° C. The wet-cake was returned to a speck free 12 L 3-neck round-bottom flask and speck free ethyl acetate (4.4 L) was added. The slurry was heated to at least 75° C. and held for at least 2 hours. The reaction was cooled to at least 30° C. and the solids were filtered on a speck free filter. The solids were washed with speck free ethyl acetate (1.6 L). The wet-cake was returned to the same speck free 12 L 3-neck round-bottom flask and speck free ethyl acetate (4.4 L) was added. The slurry was heated to at least 75° C. and held for at least 2 hours. The reaction was cooled to at least 30° C. and the solids were filtered on a speck free filter. The solids were washed with speck free ethyl acetate (1.6 L). The product was dried at 45° C. to 50° C. for at least 24 hours to yield 289 g the title product, Polymorph Form A (41.4% yield, 98.68% purity by HPLC).

The particle size generated by the above methodology generates a particle size that does not require milling. A simple hand-sieving process removed any lumps. The product (289 g) was hand sieved through a speck free #25 hand sieve with 0.0278-inch openings. 277 g of material were obtained.

Alternatively, Polymorph Form A may be prepared by conversion of Polymorph Form B according to the following procedures:

Example 5

N-[({2-[4-(2-Ethyl-4,6-dimethyl-1H-imidazo[4,5-c] pyridin-1-yl)phenyl]ethyl}amino)carbonyl]-4-methylbenzenesulfonamide Polymorph Form A

Acetonitrile (79.50 L, 62.01 kg, 1510 moles) was added to N-[({2-[4-(2-ethyl-4,6-dimethyl-1H-imidazo[4,5-c]pyridin-1-yl)phenyl]ethyl}amino)carbonyl]-4-methylbenzenesulfonamide Polymorph Form B (5.300 kg, 10.78 moles) while keeping the temperature at 20 to 30° C. The mixture was heated to a temperature of 75 to 85° C., giving a clear solution, then cooled from 80° C. to a temperature of 35 to 45° C. over a period of 10 to 50 minutes. The material was concentrated until the lowest stirrable volume was reached. Ethyl acetate (79.50 L, 70.75 kg, 803.1 moles) was added while keeping the temperature at 20 to 30° C., then the material was concentrated and the condensate collected (about 79.50 L). Ethyl acetate (79.50 L, 70.75 kg, 803.1) was added while keeping the temperature at 20 to 30° C., then the material was concentrate and the condensate collected (about 79.50 L). The material was cooled from 80° C. to a temperature of 15 to 35° C., filtered, rinsed with ethyl acetate and dried. N-[({2-[4-(2-ethyl-4,6-dimethyl-1H-imidazo[4,5-c]pyridin-1-yl) phenyl]ethyl}amino)carbonyl]-4-methylbenzenesulfonamide Polymorph Form A was isolated and dried at 35 to 45° C. for 12 to 132 hr to give 4.929 kg (93.00%).

Example 6

N-[({2-[4-(2-Ethyl-4,6-dimethyl-1H-imidazo[4,5-c] pyridin-1-yl)phenyl]ethyl}amino)carbonyl]-4-methylbenzenesulfonamide Polymorph Form A

Approximately 30 volumes of ethanol was added to one gram of N-[({2-[4-(2-ethyl-4,6-dimethyl-1H-imidazo[4,5-c]pyridin-1-yl)phenyl]ethyl}amino)carbonyl]-4-methylbenzenesulfonamide Polymorph Form B. The material dissolved to form a solution at ambient temperature. Approximately half of the solvent was distilled by rotary evaporation to the point at which oil began to form on the sides of the flask. The solution was seeded with Polymorph Form A crystals and stirred at ambient temperature overnight. The next day, the solution was cooled in an ice water bath and vacuum filtered. The yield was approximately 63%.

Example 7

N-[({2-[4-(2-Ethyl-4,6-dimethyl-1H-imidazo[4,5-c] pyridin-1-yl)phenyl]ethyl}amino)carbonyl]-4-methylbenzenesulfonamide Polymorph Form B

An inertized glass lined 100 L reactor was charged with 2-[4-(2-ethyl-4,6-dimethyl-1H-imidazo[4,5-c]pyridin-1-yl) phenyl]ethylamine (4.24 kg) followed by $CH_2Cl_2$ (34 L) to give a slightly turbid solution. To remove traces of the corresponding hydrochloride salt, the solution was filtered through an in-line filter and the reactor/filter was rinsed with $CH_2Cl_2$ (4 L). Toluenesulfonylisocyanate (2.78 kg) was transferred into a dropping funnel and the lines were rinsed with $CH_2Cl_2$ (2 L). The isocyanate solution was added over 30 min to the solution of the starting material, keeping the temperature between 17-22° C. After half of the solution was added, a thick suspension was formed. At the end of the dosage a clear, yellow solution was obtained again. The dropping funnel was rinsed with $CH_2Cl_2$ (1 L). An aliquot was drawn and showed 97.41% a/a (HPLC) of product besides 0.44% a/a (HPLC) of starting material. The product solution was transferred into a barrel and the reactor was cleaned with inline-filtered solvents. A particle determination showed the reactor to be particle free. The product solution was inline-filtered and transferred into the reactor. $CH_2Cl_2$ was distilled off at 55° C. jacket temperature and 450-400 mbar while inline-filtered acetone (46 L) was added. After distillation of 59 L of solvents the second portion of acetone (47 L) was slowly added.

After the distillation of 94 L at IT=25° C., the product started to precipitate. After a total of 121 L of solvents were distilled off, the vacuum was broken with $N_2$ and an aliquot was drawn. NMR showed about 0.24 mol % residual $CH_2Cl_2$ relative to acetone. The suspension was stirred at 20° C. for 13 h, then it was cooled to 0° C. and stirred for 2 h at this temperature. The mixture was filtered and the filter-cake was washed twice with ice-cold acetone (2×10.5 L). The product was dried at 70° C. bath temperature and 11 mbar for about 100 h.

Alternatively, Polymorph Forms B and A may be prepared according to the following procedures:

Example 8

N-[({2-[4-(2-Ethyl-4,6-dimethyl-1H-imidazo[4,5-c]pyridin-1-yl)phenyl]ethyl}amino)carbonyl]-4-methylbenzenesulfonamide Polymorph Form B and conversion to Polymorph Form A Step 1: Benzyl 4-(2,6-dimethyl-3-nitropyridin-4-ylamino)phenethylcarbamate hydrochloride To a clean and dry, nitrogen-purged 1 L round-bottom were charged tetra-N-butylammonium bromide (1.24 g, 3.85 mmoles) and 2-methyltetrahydrofuran (350 mL). 4-(2-Aminoethyl)benzenamine (35.0 g, 257 mmoles) was then added as a melt. This was followed by addition of a solution of sodium hydroxide (51.4 g, 1280 mmoles) dissolved in water (350 mL) keeping the temperature below 30° C. The reaction was then cooled to between −5° C. and 5° C. After holding for at least 30 minutes between −5° C. and 5° C., benzyl chloroformate (43.8 g, 257 mmoles) was added keeping the temperature between −50° C. and 5° C. The reaction was heated to between 0° C. and 10° C. and held for at least 30 minutes until deemed complete by HPLC. After warming the reaction to between 20° C. and 30° C., the reaction was allowed to settle for at least 60 minutes and then the phases were split. Citric acid (54.0 g, 257 mmoles) dissolved in water (350 mL) was added to the organic layer. After stirring for at least 60 minutes between 20° C. and 30° C. the phases were allowed to settle for at least 2 hours. The phases were split and the organic solution of benzyl 4-aminophenethylcarbamate was set aside. 4-Chloro-2,6-dimethyl-3-nitropyridine (40.0 g, 214 mmoles) was added to the now empty flask followed by the addition of the organic layer containing the benzyl 4-aminophenethylcarbamate and 2-propanol (350 mL). The reaction was heated to between 70° C. and 80° C. for at least 2 hours until the reaction was deemed complete by HPLC. The 2-propanol was displaced atmospherically with 2-methyltetrahydrofuran to a final volume of approximately 350 mL. The reaction was then cooled to between 15° C. and 25° C. and a sample was pulled for KF and GC Headspace. The reaction was held between 15° C. and 25° C. for at least 6 hours and the reaction was filtered and washed with 2-methyltetrahydrofuran (105 mL). After blowing the cake with nitrogen for at least 2 hours and drying under vacuum with nitrogen bleed at 40° C. to 50° C. for at least 24 hours, 76.7 g (168 mmoles) of benzyl 4-(2,6-dimethyl-3-nitropyridin-4-ylamino)phenethylcarbamate hydrochloride was isolated in 78.4% yield.

Step 2: Benzyl 4-(3-amino-2,6-dimethylpyridin-4-ylamino)phenethylcarbamate hydrochloride To a clean, nitrogen-purged 1 L hydrogenation reactor were charged 5% Pt/C (625 mg), benzyl 4-(2,6-dimethyl-3-nitropyridin-4-ylamino)phenethylcarbamate hydrochloride (25.0 g, 54.7 mmoles) and methanol (550 mL). The reaction was stirred for at least 15 minutes and then purged sequentially with nitrogen and hydrogen. The reaction was then pressurized with hydrogen to between 18 and 25 psi at between 22° C. and 28° C. until HPLC showed no starting material remained. The reaction was purged with nitrogen and the catalyst was filtered on a water-wet celite-coated filter and the cake was washed with methanol (125 mL). The resulting solution of benzyl 4-(3-amino-2,6-dimethylpyridin-4-ylamino)phenethylcarbamate hydrochloride was transferred to a clean and dry nitrogen-purged 1 L round-bottom flask. Methanol was displaced atmospherically with 2-propanol to a final volume of approximately 125 mL. The reaction was then cooled to between 15° C. and 25° C. over at least 60 minutes and sampled for KF. The reaction was then filtered and washed with 2-propanol (75 mL). After blowing the cake with nitrogen for at least 15 minutes and drying under vacuum at 40° C. to 50° C. with nitrogen bleed for at least 12 hours, 21.0 g (49.2 mmoles) of benzyl 4-(3-amino-2,6-dimethylpyridin-4-ylamino)phenethylcarbamate hydrochloride was isolated in 89.9% yield.

Step 3: 2-(4-(2-Ethyl-4,6-dimethyl-1H-imidazo[4,5-c]pyridin-1-yl)phenyl)ethanamine hydrochloride To a clean and dry, nitrogen-purged 1 L round-bottom flask were charged benzyl 4-(3-amino-2,6-dimethylpyridin-4-ylamino)phenethylcarbamate hydrochloride (30.0 g, 70.3 mmoles), 2-methyltetrahydrofuran (150 mL), triethylamine (14.9 g, 148 mmoles) and propionic anhydride (11.9 g, 91.3 mmoles) all at 20° C. to 25° C. The reaction was then heated to between 70° C. and 80° C. for at least 6 hours. After cooling to between 20° C. and 25° C. the reaction was sampled and deemed complete by HPLC. The reaction was then quenched with sodium hydroxide (8.4 g, 211 mmoles) dissolved in water (150 mL) keeping the temperature below 30° C. After holding the reaction between 20° C. and 25° C. for at least 30 minutes the reaction was allowed to settle for at least 60 minutes. The phases were separated and 2-methyltetrahydrofuran was used to atmospherically remove trace triethylamine until a final volume of approximately 180 mL was achieved. The resulting solution of benzyl 2-(4-(2-ethyl-4,6-dimethyl-1H-imidazo[4,5-c]pyridin-1-yl)phenyl)ethylcarbamate was transferred to a clean, nitrogen-purged 1 L hydrogenation reactor containing 10% Pd/C (1.5 g), and methanol (120 mL). The reaction was stirred for at least 15 minutes and then purged sequentially with nitrogen and hydrogen. The reaction was heated to between 45° C. and 55° C. and then pressurized with hydrogen to between 45 and 55 psi. After stirring at temperature and pressure for 18 hours the reaction was cooled and sampled for reaction completion. The reaction was deemed complete by HPLC and was filtered through a water-wet celite-coated filter. The filter was then washed with methanol (195 mL) and the resulting solution of 2-(4-(2-ethyl-4,6-dimethyl-1H-imidazo[4,5-c]pyridin-1-yl)phenyl)ethanamine was transferred to a clean and dry nitrogen-purged 1 L round-bottom flask then concentrated hydrochloric acid (6.3 mL, 73.8 mmoles) was added. Methanol was then removed atmospherically with 2-methylterahydrofuran until low water levels were achieved. The solvent levels were then adjusted to achieve the desired 4:1 ratio of 2-methyltetrahydrofuran:methanol (10 volumes total). The reaction was then heated to between 60° C. and 70° C. for at least 2 hours. After cooling to between 15° C. and 25° C. over at least 60 minutes the reaction was held between 15° C. and 25° C. for at least 60 minutes. The reaction was then filtered and the cake washed with 2-methyltetrahydrofuran (90 mL).

After blowing the cake with nitrogen for at least 2 hours the solids were returned to the same reactor and 2-methyltetrahydrofuran (240 mL) and methanol (60 mL) were added. The reaction was heated to between 60° C. and 70° C. and held at temperature for at least 2 hours. After cooling to between 150° C. and 25° C. over a minimum of 60 minutes the reaction was held at temperature for at least 60 minutes. The reaction was then filtered and the cake washed with 2-methyltetrahydrofuran (90 mL). After drying under vacuum between 40° C. and 50° C. for a minimum of 12 hours with a slight nitrogen bleed 21.0 g (63.5 mmoles) of 2-(4-(2-ethyl-4,6-dimethyl-1H-imidazo[4,5-c]pyridin-1-yl)phenyl)ethanamine hydrochloride was isolated in 90.3% yield.

Step 4: N-[({2-[4-(2-Ethyl-4,6-dimethyl-1H-imidazo[4,5-c]pyridin-1-yl)phenyl]ethyl}amino)carbonyl]-4-methylbenzenesulfonamide Polymorph Form B To a clean and dry nitrogen-purged 500 mL round-bottom flask were charged 2-(4-(2-ethyl-4,6-dimethyl-1H-imidazo[4,5-c]pyridin-1-yl)phenyl)ethanamine hydrochloride (40.0 g, 121 mmoles), dichloromethane (400 mL) and sodium hydroxide (9.7 g, 242 mmoles) diluted with water (400 mL) such that the temperature remains below 30° C. The reaction was held at this temperature for a minimum of 30 minutes and then allowed to settle for at least 60 minutes. The phases were separated and the aqueous layer stirred with dichloromethane (400 mL) for at least 30 minutes below 30° C. and then allowed to settle for at least 60 minutes. The phases were separated and dichloromethane was used to atmospherically remove excess water from the combined organic layers to a final volume of approximately 800 mL. The reaction was filtered and transferred to a 2 L round-bottom flask. Toluenesulfonylisocyanate (23.8 g, 121 mmoles) was added to the filtrate over a minimum of 30 minutes keeping the temperature between 10° C. and 25° C. After holding the reaction between 10° C. and 25° C. for a minimum of 30 minutes, the reaction was deemed complete by HPLC. Acetone was used to atmospherically displace the dichloromethane to low levels and final reaction volume was approximately 240 mL. The reaction was cooled to between 20° C. and 30° C. over a minimum of 2 hours and the reaction was sampled. The sample showed polymorph B was present and the reaction was then cooled to between −5° C. and −25° C. for a minimum of 2 hours. The reaction was filtered and washed with acetone (80 mL, 2 times) cooled to between −5° C. and −25° C. The cake was held under a stream of nitrogen on the filter for at least 12 hours. After this time the cake was deemed dry and 49.6 g (101 mmoles) of N-[({2-[4-(2-ethyl-4,6-dimethyl-1H-imidazo[4,5-c]pyridin-1-yl)phenyl]ethyl}amino)carbonyl]-4-methylbenzenesulfonamide Polymorph Form B were collected for at 83.4% yield.

Step 5: N-[({2-[4-(2-Ethyl-4,6-dimethyl-1H-imidazo[4,5-c]pyridin-1-yl)phenyl]ethyl}amino)carbonyl]-4-methylbenzenesulfonamide Polymorph Form A To a clean and dry, nitrogen-purged, 1 L round-bottom flask were charged N-[({2-[4-(2-ethyl-4,6-dimethyl-1H-imidazo[4,5-c]pyridin-1-yl)phenyl]ethyl}amino)carbonyl]-4-methylbenzenesulfonamide Polymorph Form B (30.0 g, 61.0 mmoles) and acetonitrile (600 mL). The reaction was then heated to gentle column reflux to achieve homogeneity. After holding the reaction at reflux for at least 60 minutes, the reaction was concentrated to approximately 450 mL. The reaction was then cooled to between 20° C. and 30° C. in less than 90 minutes. The reaction was held at 30° C. overnight and sampled showing conversion to Form A. Acetonitrile was displaced with ethyl acetate under vacuum until a final volume of approximately 300 mL remains. The reaction was heated to gentle column reflux and the solids allowed to granulate at temperature for at least 6 hours. The reaction was cooled to between 18° C. and 22° C. and allowed to stir at temperature for at least 2 hours. The reaction was filtered and washed with ethyl acetate (90 mL). After drying under vacuum between 40° C. and 50° C. for a minimum of 12 hours with a slight nitrogen bleed, 27.0 g (54.9 mmoles) of N-[({2-[4-(2-ethyl-4,6-dimethyl-1H-imidazo[4,5-c]pyridin-1-yl)phenyl]ethyl}amino)carbonyl]-4-methylbenzenesulfonamide Polymorph Form A were collected for a 90.0% yield.

Example 9

Direct isolation of N-[({2-[4-(2-ethyl-4,6-dimethyl-1H-imidazo[4,5-c]pyridin-1-yl)phenyl]ethyl}amino)carbonyl]-4-methylbenzenesulfonamide Polymorph Form A To a clean and dry, nitrogen-purged 250 mL round-bottom flask were charged 2-(4-(2-ethyl-4,6-dimethyl-1H-imidazo[4,5-c]pyridin-1-yl)phenyl)ethanamine (11.0 g, 37.2 mmoles) and dichloromethane (110 mL). Toluenesulfonylisocyanate (7.3 g, 37.2 mmoles) was added over a minimum of 30 minutes keeping the temperature between 10° C. and 25° C. After holding the reaction between 10° C. and 25° C. for a minimum of 30 minutes, the reaction was deemed complete by HPLC. Activated charcoal (DARCO, 110 mg) was added and stirred for at least 15 minutes. The reaction was filtered and transferred to a 150 mL round-bottom flask. Acetone was used to atmospherically displace the dichloromethane to low levels and final reaction volume was approximately 30 mL. The reaction was cooled to between 20° C. and 30° C. and seeded with N-[({2-[4-(2-ethyl-4,6-dimethyl-1H-imidazo[4,5-c]pyridin-1-yl)phenyl]ethyl}amino)carbonyl]-4-methylbenzenesulfonamide Polymorph Form A (219 mg). The reaction was allowed to granulate for at least 12 hours between 20° C. and 30° C. The reaction was then cooled to between −5° C. and 5° C. for a minimum of 2 hours. The reaction was filtered and washed with acetone (40 mL) cooled to between −5° C. and 5° C. The cake was held under a stream of nitrogen on the filter for at least 12 hours. After this time 1.8 g (3.66 mmole) of N-[({2-[4-(2-ethyl-4,6-dimethyl-1H-imidazo[4,5-c]pyridin-1-yl)phenyl]ethyl}amino)carbonyl]-4-methylbenzenesulfonamide Polymorph Form A were collected for a 9.8% yield.

Example 10

N-[({2-[4-(2-Ethyl-4,6-dimethyl-1H-imidazo[4,5-c]pyridin-1-yl)phenyl]ethyl}amino)carbonyl]-4-methylbenzenesulfonamide Crystal Form C Crystal Form C was obtained by crystallisation from a solution of N-[({2-[4-(2-Ethyl-4,6-dimethyl-1H-imidazo[4,5-c]pyridin-1-yl)phenyl]ethyl}amino)carbonyl]-4-methylbenzenesulfonamide in a mixture of chloroform and ethyl acetate.

Example 11

N-[({2-[4-(2-Ethyl-4,6-dimethyl-1H-imidazo[4,5-c]pyridin-1-yl)phenyl]ethyl}amino)carbonyl]-4-methylbenzenesulfonamide Crystal Form D Crystal Form D was obtained by crystallisation from a water slurry of N-[({2-[4-(2-Ethyl-4,6-dimethyl-1H-imidazo[4,5-c]pyridin-1-yl)phenyl]ethyl}amino)carbonyl]-4-methylbenzenesulfonamide.

Example 12

N-[({2-[4-(2-Ethyl-4,6-dimethyl-1H-imidazo[4,5-c]pyridin-1-yl)phenyl]ethyl}amino)carbonyl]-4-methylbenzenesulfonamide Crystal Form G Crystal Form G was observed at elevated temperatures while analyzing Crystal Form D by VT-XPRD. Crystal Form G was not observed at ambient temperature.

Analytical Data

X-Ray Powder Diffraction

The comparative PXRD analyses of Polymorph Forms A and B and the reference sample from WO 02/32900, Example 42, Step 8 (see present Example 2 and FIG. 6) were performed using a Rigaku RINT-TTR X-ray powder diffractometer using Cu-Kα radiation. The instrument is equipped with a fine focus X-ray tube. The tube voltage and amperage were set to 50 kV and 300 mA respectively. The divergence and scattering slits were set at 0.25° and the receiving slit was set at 0.15 mm. Diffracted radiation was detected by a NaI scintillation detector. A theta-two theta continuous scan at 4°/min (0.3 sec/0.02° step) from 3 to 30° 2θ was used. A silicon standard was analyzed to check the machine alignment. Data were collected and analyzed using-Rigaku X-ray system. Samples were prepared for analysis by placing them in an aluminium sample holder that is horizontally rotated at 60 rpm during data acquisition.

The PXRD analyses of Polymorph Forms A and B and Crystal Forms C, D and G, shown in FIGS. 1 to 5, were performed according to the following method:

Powder X-Ray Diffraction Analysis

The powder patterns were collected using a Bruker D5000 diffractometer equipped with copper radiation, fixed slits (1.0, 1.0, 0.6 mm), and a Kevex or Sol-X solid state detector. Data was collected from 3.0 to 40.0 degrees in two theta using a step size of 0.04 degree and a step time of 1.0 second.

Single Crystal X-Ray Analysis

Data was collected at room temperature using Bruker X-ray diffractometers equipped with copper radiation and graphite monochromators. Structures were solved using direct methods. The SHELXTL* computer library provided by Bruker AXS, Inc facilitated all necessary crystallographic computations and molecular displays.

*The SHELXTL computer library has been developed and upgraded over a long period of time. The most recent version of this work in progress is as follows: SHELXTL™ Reference Manual, Version 5.1, Bruker AXS, Madison, Wis., USA (1997).

Calculation of PXRD Pattern from Single Crystal Data

To compare the results between a single crystal and a powder sample, a calculated powder pattern can be obtained from single crystal results. The XFOG and XPOW computer programs provided as part of the SHELXTL* computer library can perform this calculation. Comparing the calculated powder pattern with the experimental powder pattern will confirm whether a powder sample corresponds to an assigned single crystal structure. This procedure has been performed on N-[({2-[4-(2-Ethyl-4,6-dimethyl-1H-imidazo[4,5-c]pyridin-1-yl)phenyl]ethyl}amino)carbonyl]-4-methylbenzenesulfonamide Polymorph Form A, and Crystal Form D. A match between the two patterns indicated the agreement between powder sample and the corresponding single crystal structure.

Figure 1A:
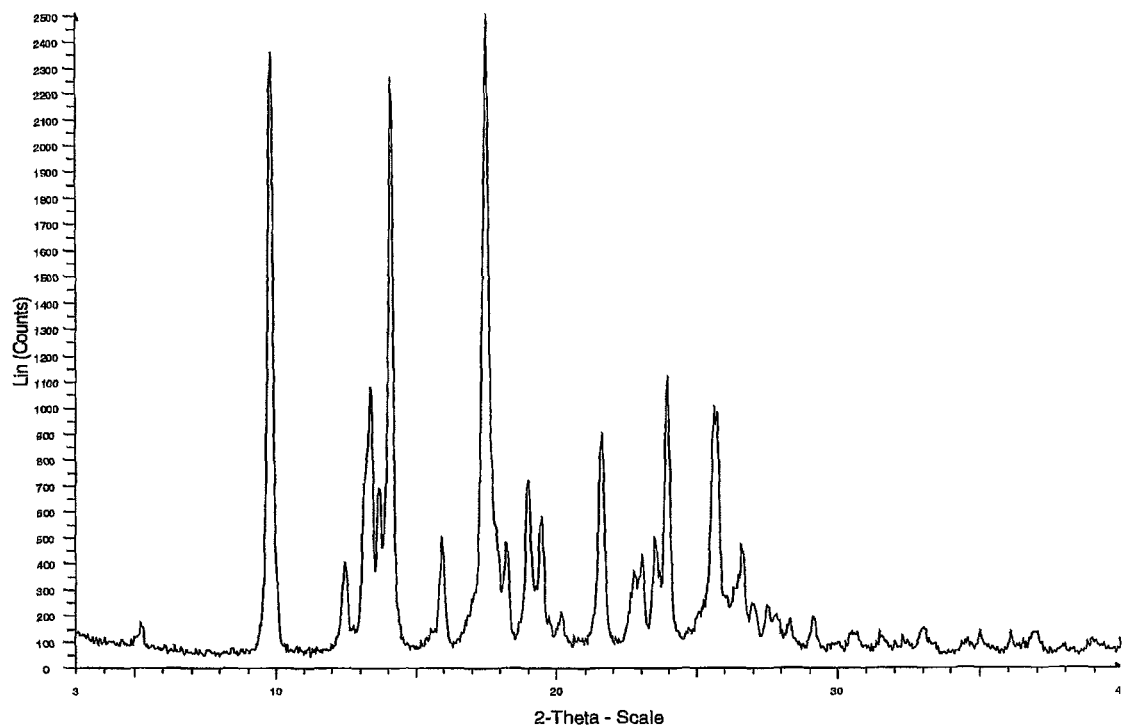
FIG. 1a shows the PXRD pattern of N-[({2-[4-(2-Ethyl-4,6-dimethyl-1H-imidazo[4,5-c]pyridin-1-yl)phenyl]ethyl}amino)carbonyl]-4-methylbenzenesulfonamide Polymorph Form A.
Figure 1B:
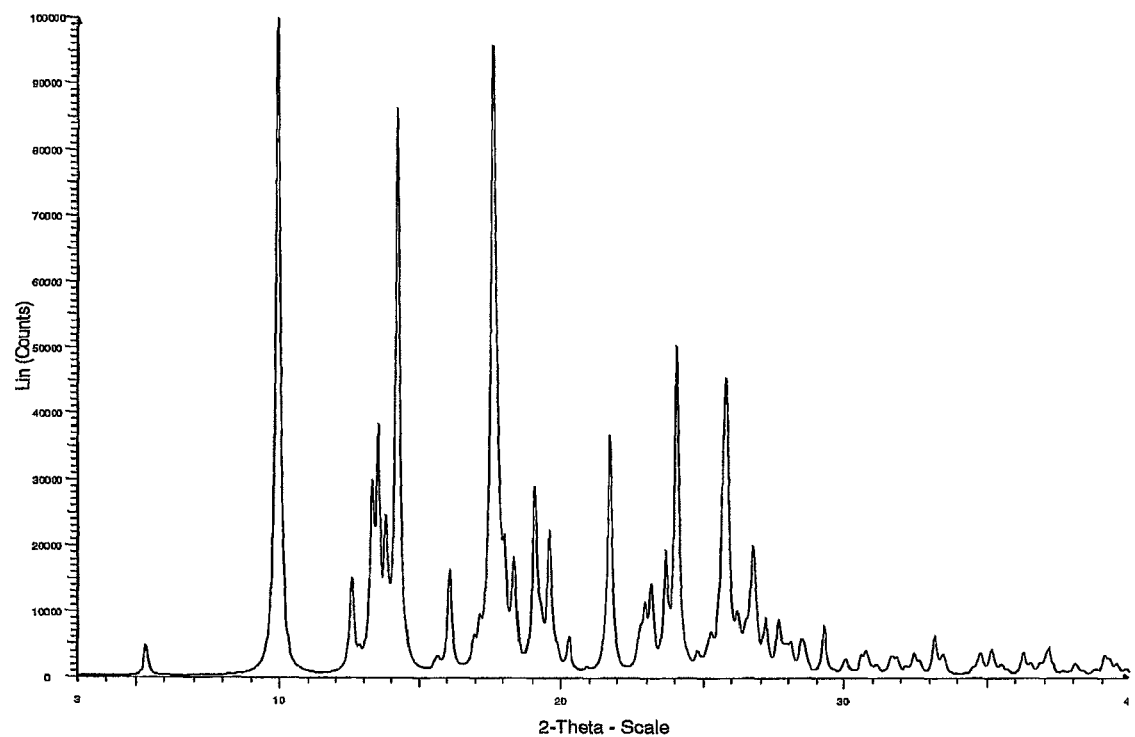
FIG. 1b shows the calculated PXRD pattern of N-[({2-[4-(2-Ethyl-4,6-dimethyl-1H-imidazo[4,5-c]pyridin-1-yl)phenyl]ethyl}amino)carbonyl]-4-methylbenzenesulfonamide Polymorph Form A.
Figure 2:
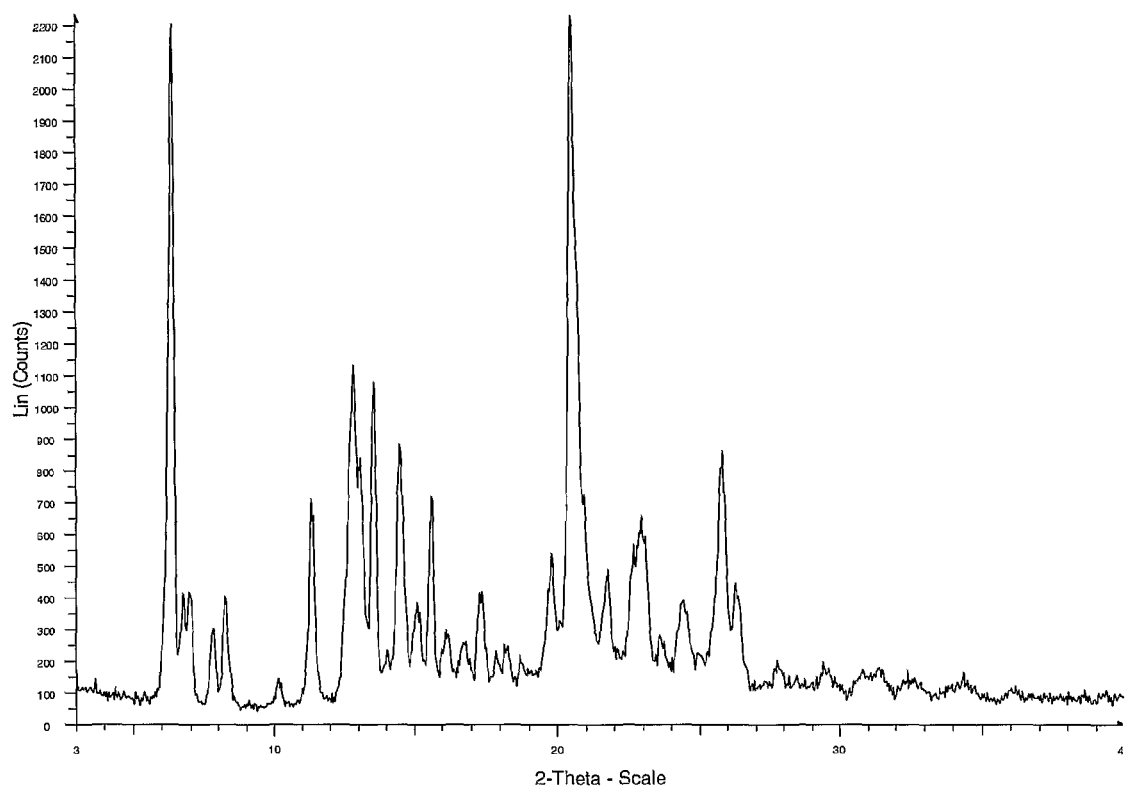
FIG. 2 shows the PXRD pattern of N-[({2-[4-(2-Ethyl-4,6-dimethyl-1H-imidazo[4,5-c]pyridin-1-yl)phenyl]ethyl}amino)carbonyl]-4-methylbenzenesulfonamide Polymorph Form B.
Figure 3:
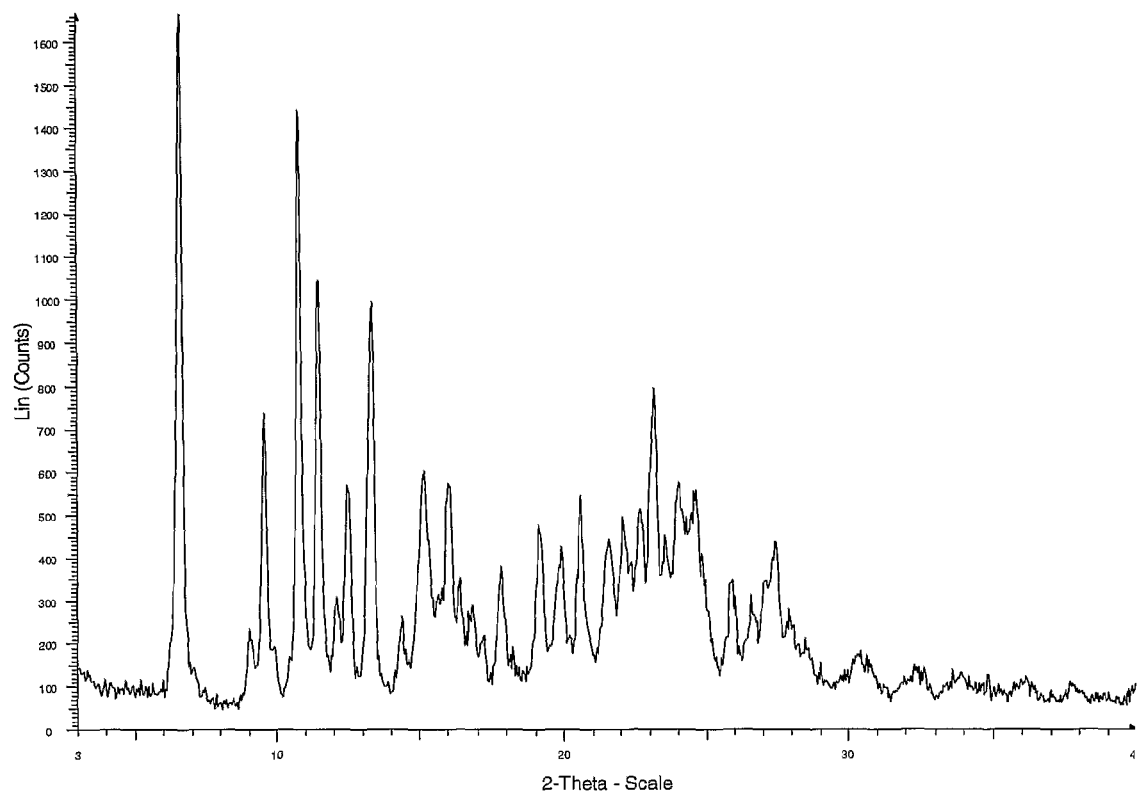
FIG. 3 shows the PXRD pattern of N-[({2-[4-(2-Ethyl-4,6-dimethyl-1H-imidazo[4,5-c]pyridin-1-yl)phenyl]ethyl}amino)carbonyl]-4-methylbenzenesulfonamide Crystal Form C.
Figure 4A:
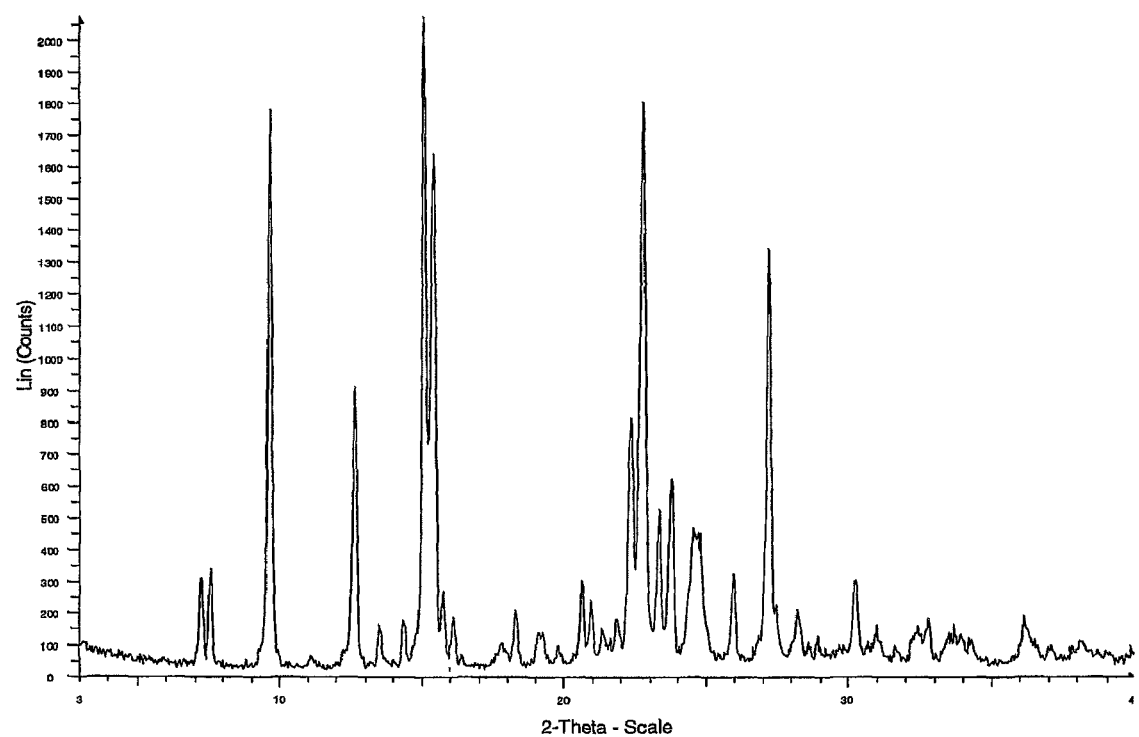
FIG. 4a shows the PXRD pattern of N-[({2-[4-(2-Ethyl-4,6-dimethyl-1H-imidazo[4,5-c]pyridin-1-yl)phenyl]ethyl}amino)carbonyl]-4-methylbenzenesulfonamide Crystal Form D.
Figure 4B:
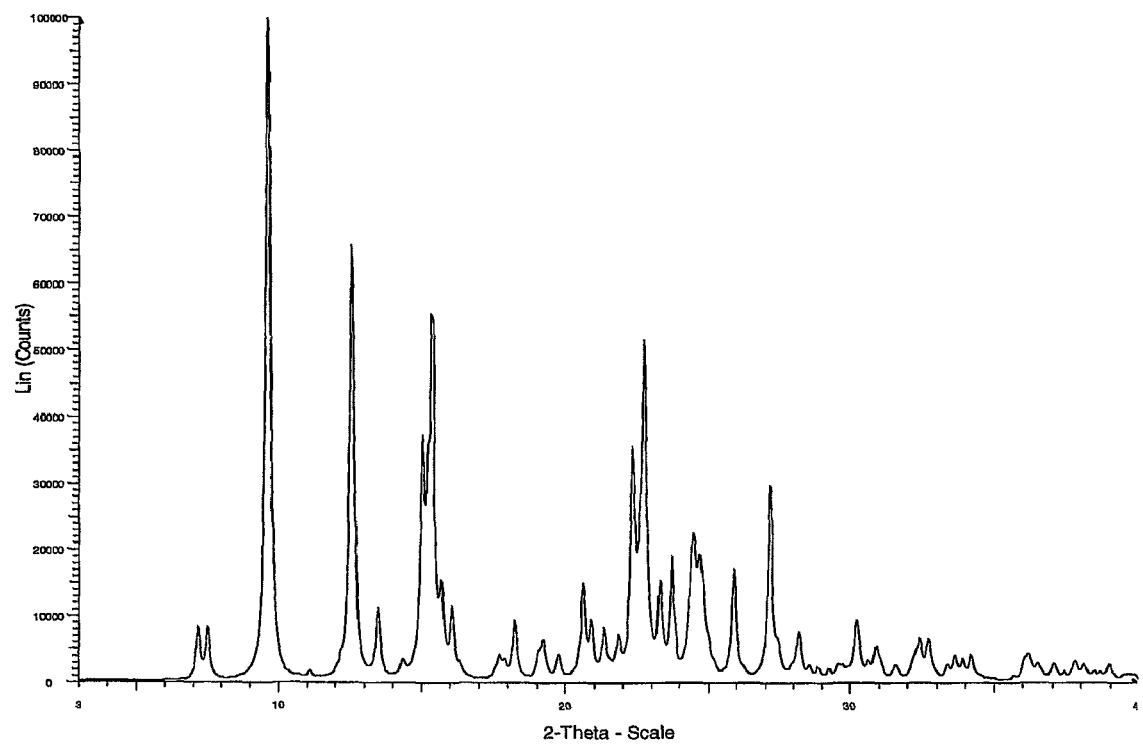
FIG. 4b shows the calculated PXRD pattern of N-[({2-[4-(2-Ethyl-4,6-dimethyl-1H-imidazo[4,5-c]pyridin-1-yl)phenyl]ethyl}amino)carbonyl]-4-methylbenzenesulfonamide Crystal Form D.
Figure 5:
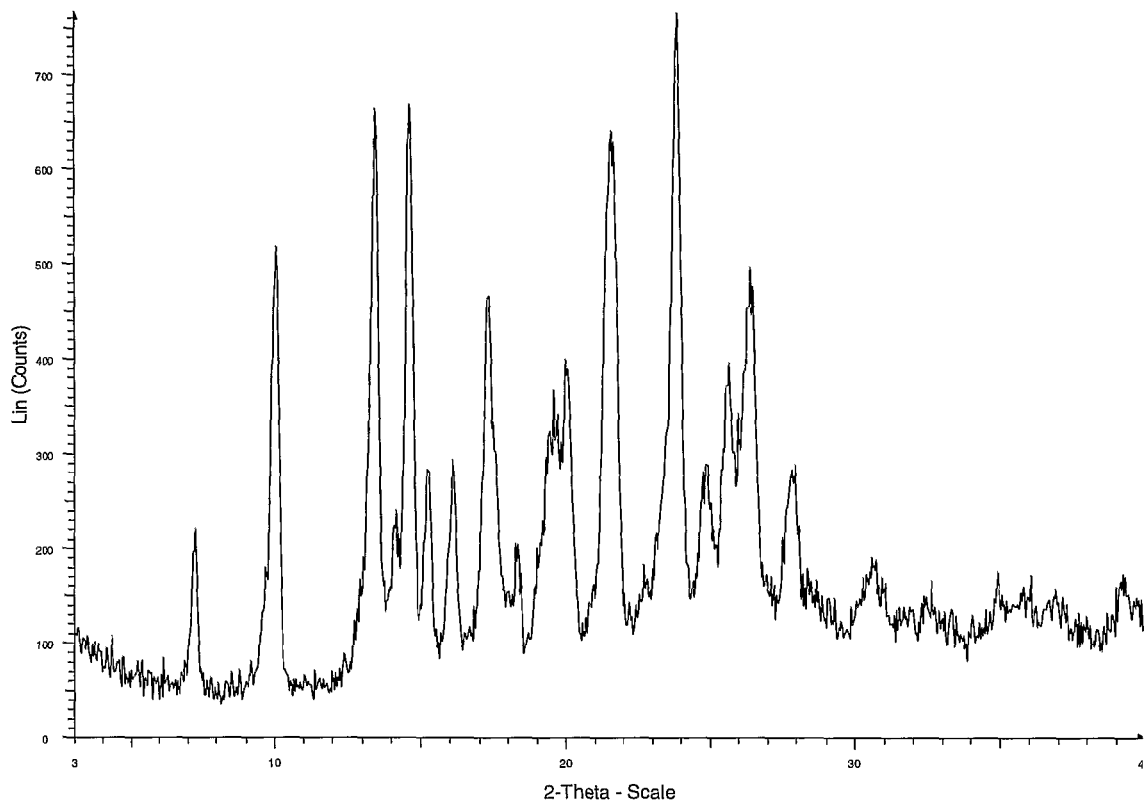
FIG. 5 shows the PXRD pattern of N-[({2-[4-(2-Ethyl-4,6-dimethyl-1H-imidazo[4,5-c]pyridin-1-yl)phenyl]ethyl}amino)carbonyl]-4-methylbenzenesulfonamide Crystal Form G.
Figure 6:
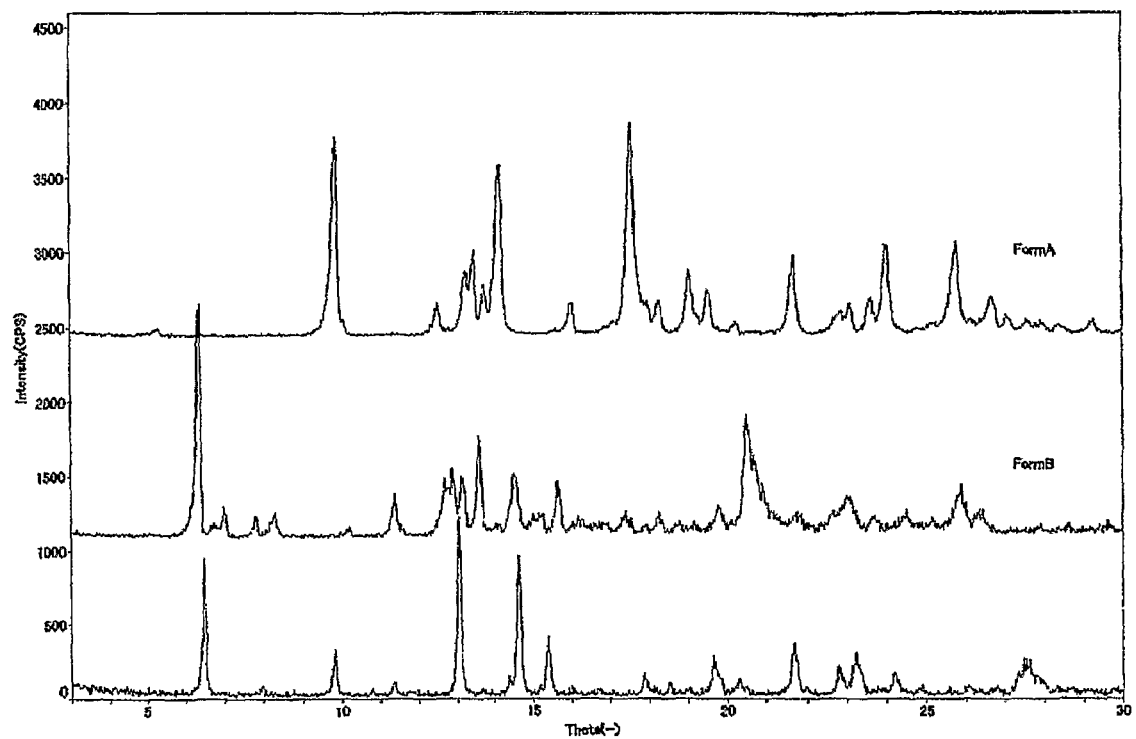

FIG. 6 shows a comparison of the PXRD patterns of Polymorph Forms A and B and a reference product obtained from the method of preparing N-[({2-[4-(2-Ethyl-4,6-dimethyl-1H-imidazo[4,5-c]pyridin-1-yl)phenyl]ethyl}amino)carbonyl]-4-methylbenzenesulfonamide described in WO 02/32900, Example 42, Step 8 (see present Example 2). This comparative chart shows that Polymorph Forms A and B do not correspond to the reference product described in WO 02/32900 and are therefore distinct novel polymorphic forms.

The peak listings for the above figures are given in table 2. Peak intensity is dependent on the morphology and particle size of a sample and may vary, with low intensity peaks (intensity less than 10%) being absent in some cases.

TABLE 2

| POLYMORPH FORM A | | POLYMORPH FORM B | |
|---|---|---|---|
| Angle 2-Theta ° +/− 0.2 | Intensity % | Angle 2-Theta ° +/− 0.2 | Intensity % |
| 5.2 | 6.9 | 6.3 | 98.8 |
| 9.8 | 94.1 | 6.7 | 18.3 |
| 12.5 | 15.9 | 7.0 | 18.5 |
| 13.2 | 33.2 | 7.8 | 13.5 |
| 13.4 | 43 | 8.2 | 18.0 |
| 13.7 | 27.5 | 10.1 | 6.2 |
| 14.1 | 90.3 | 11.3 | 31.7 |
| 15.6 | 5.9 | 12.8 | 50.6 |
| 15.9 | 19.9 | 13.0 | 37.7 |
| 17.1 | 10.2 | 13.5 | 48.0 |
| 17.5 | 100 | 14.0 | 10.3 |
| 17.8 | 21.8 | 14.5 | 39.4 |
| 18.2 | 19.1 | 15.1 | 17.1 |

TABLE 2-continued

| Angle 2-Theta° +/- 0.2 | Intensity % | Angle 2-Theta° +/- 0.2 | Intensity % |
|---|---|---|---|
| 19.0 | 28.8 | 15.6 | 32.1 |
| 19.5 | 23.1 | 16.2 | 12.6 |
| 20.2 | 8.4 | 16.8 | 11.6 |
| 21.6 | 35.9 | 17.3 | 18.6 |
| 22.8 | 14.7 | 17.9 | 10.2 |
| 23.0 | 17.2 | 18.2 | 10.9 |
| 23.5 | 19.8 | 18.3 | 10.9 |
| 24.0 | 44.7 | 18.8 | 9.6 |
| 24.8 | 5.9 | 19.8 | 24.0 |
| 25.1 | 8.5 | 20.5 | 100.0 |
| 25.7 | 40 | 21.0 | 32.2 |
| 26.1 | 11 | 21.8 | 21.8 |
| 26.6 | 18.7 | 22.7 | 25.2 |
| 27.0 | 9.7 | 23.0 | 29.4 |
| 27.5 | 9.5 | 23.6 | 12.5 |
| 27.8 | 8 | 24.4 | 17.3 |
| 28.3 | 7.3 | 25.0 | 10.1 |
| 29.2 | 7.6 | 25.8 | 38.5 |
| 30.5 | 5.4 | 26.3 | 19.9 |
| 31.6 | 5.4 | 27.8 | 8.9 |
| 32.3 | 4.7 | 29.4 | 8.7 |
| 33.1 | 6 | 30.8 | 7.7 |
| 34.6 | 4.3 | 31.4 | 7.9 |
| 35.1 | 5.5 | | |
| 36.1 | 5.3 | | |
| 37.0 | 5.3 | | |

CRYSTAL FORM C / CRYSTAL FORM D

| CRYSTAL FORM C | | CRYSTAL FORM D | |
|---|---|---|---|
| Angle 2-Theta° +/- 0.2 | Intensity % | Angle 2-Theta° +/- 0.2 | Intensity % |
| 6.6 | 100.0 | 7.2 | 14.8 |
| 7.1 | 8.4 | 7.6 | 16.0 |
| 7.5 | 5.8 | 9.6 | 85.7 |
| 9.0 | 13.8 | 11.1 | 3.1 |
| 9.5 | 44.0 | 12.6 | 43.8 |
| 9.9 | 11.4 | 13.5 | 7.5 |
| 10.8 | 86.3 | 14.4 | 8.3 |
| 11.5 | 62.6 | 15.1 | 100.0 |
| 12.1 | 18.4 | 15.4 | 79.0 |
| 12.5 | 33.9 | 15.7 | 12.8 |
| 13.3 | 59.5 | 16.1 | 8.8 |
| 14.4 | 15.6 | 17.8 | 5.0 |
| 15.2 | 36.1 | 18.3 | 9.9 |
| 15.4 | 26.8 | 19.2 | 6.6 |
| 16.0 | 34.2 | 19.8 | 4.6 |
| 16.4 | 21.0 | 20.7 | 14.4 |
| 16.8 | 17.3 | 21.0 | 11.4 |
| 17.2 | 13.0 | 21.4 | 7.0 |
| 17.8 | 22.6 | 21.9 | 8.7 |
| 18.2 | 11.4 | 22.4 | 39.1 |
| 19.2 | 28.4 | 22.8 | 86.9 |
| 19.9 | 25.4 | 23.4 | 25.3 |
| 20.6 | 32.7 | 23.8 | 29.8 |
| 21.6 | 26.4 | 24.6 | 22.4 |
| 22.1 | 29.6 | 24.7 | 21.8 |
| 22.4 | 23.2 | 26.0 | 15.6 |
| 22.7 | 30.7 | 27.2 | 64.6 |
| 23.2 | 47.6 | 27.5 | 11.2 |
| 23.6 | 27.1 | 28.3 | 10.1 |
| 24.0 | 34.3 | 28.6 | 5.1 |
| 24.6 | 33.4 | 28.9 | 6.0 |
| 25.0 | 21.7 | 30.3 | 14.6 |
| 25.9 | 20.7 | 31.0 | 7.7 |
| 26.6 | 18.6 | 31.7 | 4.4 |
| 27.1 | 20.7 | 32.5 | 7.3 |
| 27.5 | 26.1 | 32.8 | 8.7 |
| 27.9 | 16.6 | 33.5 | 6.5 |
| 28.5 | 12.5 | 34.0 | 6.3 |
| 29.0 | 9.3 | 34.3 | 5.5 |
| 30.4 | 10.4 | 36.2 | 8.9 |
| 30.7 | 9.6 | | |
| 32.4 | 8.8 | | |
| 32.6 | 8.5 | | |
| 37.8 | 6.5 | | |

TABLE 2-continued

CRYSTAL FORM G

| Angle 2-Theta° +/- 0.2 | Intensity % |
|---|---|
| 7.2 | 28.7 |
| 10.0 | 67.5 |
| 13.4 | 86.7 |
| 14.1 | 31.2 |
| 14.6 | 87.2 |
| 15.3 | 36.9 |
| 16.1 | 38.2 |
| 17.3 | 60.8 |
| 18.3 | 26.6 |
| 19.6 | 41.7 |
| 20.1 | 51.9 |
| 21.6 | 83.6 |
| 22.8 | 23.7 |
| 23.1 | 28.2 |
| 23.9 | 100.0 |
| 24.8 | 37.2 |
| 24.9 | 37.7 |
| 25.7 | 51.5 |
| 26.0 | 45.0 |
| 26.4 | 64.9 |
| 27.9 | 36.9 |
| 30.7 | 24.6 |

Differential Scanning Calorimetry

Differential scanning calorimetry (DSC) was performed using a TA instrument differential scanning calorimeter 2920. The sample was placed into an aluminium DSC pan and the weight accurately recorded. The pan was either ran open or covered with a lid and then crimped. Each sample was equilibrated at 25° C. and heated under a nitrogen purge at a rate of 10° C./min, up to a final temperature of 100° C. or 350° C. One analysis was performed with an open pan and heated to 175° C. Indium metal was used as the calibration standard. Reported values are rounded and should therefore be considered approximate.

FT-IR Spectroscopy

Infrared spectra for Polymorph Form B were acquired on a Magna-IR 860® Fourier transform infrared (FT-IR) spectrophotometer (Thermo Nicolet) equipped with an Ever-Glo mid/far IR source, an extended range potassium bromide (KBr) beamsplitter, and a deuterated triglycine sulfate (DTGS) detector. A diffuse reflectance accessory (the Collector™, Thermo Spectra-Tech) was used for sampling. Each spectrum represents 256 co-added scans collected at a spectral resolution of 4 $cm^{-1}$. Sample preparation consisted of placing the sample into a 3 or 13 mm diameter cup. A background data set was acquired with an alignment mirror in place. A Log 1/R(R=reflectance) spectrum was acquired by taking a ratio of these two data sets against each other. Wavelength calibration was performed using polystyrene. Reported values are rounded and should therefore be considered approximate.

Infrared spectra for Polymorph Form A were acquired on a Shimadzu FTIR-8200PC Fourier transform infrared (FT-IR) spectrophotometer equipped with an black-coated heated wire beam source, an Germanium coated on potassium bromide (KBr) beamsplitter, and a high sensitivity pyroelectric detector (DLATGS). Each spectrum represents 40 co-added scans collected at a spectral resolution of 4 $cm^{-1}$. Sample preparation consisted of placing the KBr disk, prepared from 1 mg of the sample and 150 mg of KBr. A background data set was acquired with a blank disk of KBr without samples. A Log 1/R(R=reflectance) spectrum was acquired by taking a ratio of these two data sets against each other. Wavelength calibration was performed using polystyrene. Reported values are rounded and should therefore be considered approximate.

The invention claimed is:

1. Essentially pure, crystalline, N-[({2-[4-(2-Ethyl-4,6-dimethyl-1H-imidazo[4,5-c]pyridin-1-yl)phenyl]ethyl}amino)carbonyl]-4-methylbenzenesulfonamide Polymorph Form A, which is characterised by a powder X-ray diffraction pattern obtained by irradiation with Cu Kα radiation which includes main peaks at 2-Theta° 9.8, 13.2, 13.4, 13.7, 14.1, 17.5, 19.0, 21.6, 24.0 and 25.7+/−0.2.

2. N-[({2-[4-(2-Ethyl-4,6-dimethyl-1H-imidazo[4,5-c]pyridin-1-yl)phenyl]ethyl}amino)carbonyl]-4-methylbenzenesulfonamide Polymorph Form A as claimed in claim 1, which is further characterised by differential scanning calorimetry (DSC) in which it exhibits an endothermic event at about 160° C.

3. A pharmaceutical composition comprising N-[({2-[4-(2-Ethyl-4,6-dimethyl-1H-imidazo[4,5-c]pyridin-1-yl)phenyl]ethyl}amino)carbonyl]-4-methylbenzenesulfonamide Polymorph Form A as claimed in claim 1 or claim 2, together with one or more pharmaceutically acceptable excipients.

4. N-[({2-[4-(2-Ethyl-4,6-dimethyl-1H-imidazo[4,5-c]pyridin-1-yl)phenyl]ethyl}amino)carbonyl]-4-methylbenzenesulfonamide Polymorph Form A as claimed in claim 1 or claim 2, for use as a medicament.

5. Essentially pure, crystalline, N-[({2-[4-(2-Ethyl-4,6-dimethyl-1H-imidazo[4,5-c]pyridin-1-yl)phenyl]ethyl}amino)carbonyl]-4-methylbenzenesulfonamide Polymorph Form B, which is characterised by a powder X-ray diffraction pattern obtained by irradiation with Cu Kα radiation which includes main peaks at 2-Theta° 6.3, 11.3, 12.8, 13.0, 13.5, 14.5, 15.6, 20.5, 23.0 and 25.8+/−0.2.

6. N-[({2-[4-(2-Ethyl-4,6-dimethyl-1H-imidazo[4,5-c]pyridin-1-yl)phenyl]ethyl}amino)carbonyl]-4-methylbenzenesulfonamide Polymorph Form B as claimed in claim 5, which is further characterised by differential scanning calorimetry (DSC) in which it exhibits an endothermic event at about 178° C.

7. A pharmaceutical composition including N-[({2-[4-(2-Ethyl-4,6-dimethyl-1H-imidazo[4,5-c]pyridin-1-yl)phenyl]ethyl}amino)carbonyl]-4-methylbenzenesulfonamide Polymorph Form B as claimed in claim 5 or claim 6, together with one or more pharmaceutically acceptable excipients.

8. N-[({2-[4-(2-Ethyl-4,6-dimethyl-1H-imidazo[4,5-c]pyridin-1-yl)phenyl]ethyl}amino)carbonyl]-4-methylbenzenesulfonamide Polymorph Form B as claimed in claim 5 or claim 6 for use as a medicament.

* * * * *

UNITED STATES PATENT AND TRADEMARK OFFICE
CERTIFICATE OF CORRECTION

PATENT NO. : 7,960,407 B2
APPLICATION NO. : 11/908163
DATED : June 14, 2011
INVENTOR(S) : Naoaki Haruta et al.

It is certified that error appears in the above-identified patent and that said Letters Patent is hereby corrected as shown below:

Title Page, Item (73) should read

(73)   Assignee:  RaQualia Pharma Inc., Aichi-Ken (JP)

Signed and Sealed this
Thirtieth Day of August, 2011

David J. Kappos
*Director of the United States Patent and Trademark Office*

UNITED STATES PATENT AND TRADEMARK OFFICE
CERTIFICATE OF CORRECTION

Page 1 of 1

PATENT NO. : 7,960,407 B2
APPLICATION NO. : 11/908163
DATED : June 14, 2011
INVENTOR(S) : Naoaki Haruta et al.

It is certified that error appears in the above-identified patent and that said Letters Patent is hereby corrected as shown below:

On the Title Page

Please insert the following:

--Related U.S. Application Data

(60)  Provisional Application No. 60/660,592, filed on March 11, 2005.--

Signed and Sealed this
Second Day of August, 2016

Michelle K. Lee
*Director of the United States Patent and Trademark Office*

UNITED STATES PATENT AND TRADEMARK OFFICE

(12)     CERTIFICATE EXTENDING PATENT TERM
         UNDER 35 U.S.C. § 156

(68) PATENT NO.        :  7,960,407

(45) ISSUED            :  June 14, 2011

(75) INVENTOR          :  Naoki Haruta et al.

(73) PATENT OWNER      :  AskAt Inc.

(95) PRODUCT           :  GALLIPRANT® (grapiprant)

This is to certify that an application under 35 U.S.C. § 156 has been filed in the United States Patent and Trademark Office, requesting extension of the term of U.S. Patent No. 7,960,407 based upon the regulatory review of the product GALLIPRANT® (grapiprant) by the Food and Drug Administration. According to United States Patent and Trademark Office records, the original expiration date of the patent as of the date of issuance of this certificate is February 21, 2027. Because it appears that the requirements of the law have been met, this certificate extends the term of the patent for the period of

(94)                              870 days subject to the payment of maintenance fees as provided by law, with all rights pertaining thereto as provided by 35 U.S.C. § 156.

I have caused the seal of the United States Patent and Trademark Office to be affixed this 19th day of November 2025.

John A. Squires
Under Secretary of Commerce for Intellectual Property and
Director of the United States Patent and Trademark Office